US011721425B2

(12) United States Patent
Lazarovich

(10) Patent No.: US 11,721,425 B2
(45) Date of Patent: Aug. 8, 2023

(54) METHOD OF SYSTEM FOR INDUCING A PAVLOVIAN CONDITIONED ASSOCIATION OF AN AROMA WITH A STATE OF SATIATION

(71) Applicant: REMmedy, LLC, Stowe, VT (US)

(72) Inventor: Mark Lazarovich, Stowe, VT (US)

(73) Assignee: REMmedy, LLC, Stowe, VT (US)

( * ) Notice: Subject to any disclaimer, the term of this patent is extended or adjusted under 35 U.S.C. 154(b) by 308 days.

(21) Appl. No.: 16/948,149

(22) Filed: Sep. 4, 2020

(65) Prior Publication Data

US 2020/0402640 A1 Dec. 24, 2020

Related U.S. Application Data

(63) Continuation-in-part of application No. 16/687,738, filed on Nov. 19, 2019, now Pat. No. 10,842,433.
(Continued)

(51) Int. Cl.
*G16H 20/60* (2018.01)
*A61L 9/12* (2006.01)
(Continued)

(52) U.S. Cl.
CPC ............. *G16H 20/60* (2018.01); *A61L 9/12* (2013.01); *G16H 40/63* (2018.01);
(Continued)

(58) Field of Classification Search
CPC ............................................ A61M 21/00–02
See application file for complete search history.

(56) References Cited

U.S. PATENT DOCUMENTS 5,023,020 A 6/1991 Machida et al.
5,318,503 A 6/1994 Lord
(Continued)

FOREIGN PATENT DOCUMENTS

WO 2018108582 5/2018

OTHER PUBLICATIONS

International Search Report; PCT/US21/49128; dated Dec. 6, 2021; By Authorized Officer Kari Rodriquez.
(Continued)

*Primary Examiner* — Thaddeus B Cox
(74) *Attorney, Agent, or Firm* — Caldwell Intellectual Property Law

(57) ABSTRACT

A system for inducing a Pavlovian conditioned association of an aroma with a state of satiation, the system comprising at least a physiological sensor, wherein the at least a physiological sensor is configured to detect at least a physiological parameter of a user, and to transmit a detection signal, a control device configured to receive the detection signal from the at least a physiological sensor, wherein the control device is further configured to ascertain that the user is experiencing a physiological state associated with satiation, and to transmit the detection signal to an automatically activated scent diffuser, thereby conditioning the user to associate said scent with satiation, and an automatically activated scent diffuser, wherein the scent diffuser is configured to automatically activate upon receiving the detection signal, wherein automatically activating further comprises diffusing a scent in response to the detection signal.

20 Claims, 15 Drawing Sheets

Related U.S. Application Data

(60) Provisional application No. 62/798,659, filed on Jan. 30, 2019.

(51) Int. Cl.
  *A61M 21/00* (2006.01)
  *G16H 40/63* (2018.01)

(52) U.S. Cl.
  CPC .... *A61L 2209/111* (2013.01); *A61L 2209/134* (2013.01); *A61M 21/00* (2013.01)

(56) References Cited

U.S. PATENT DOCUMENTS

| | | |
|---|---|---|
| 6,702,767 B1 | 3/2004 | Douglas |
| 6,866,041 B2 | 3/2005 | Hardy, Jr. et al. |
| 9,434,907 B2 | 9/2016 | Jeon et al. |
| 9,511,166 B1 | 12/2016 | Li |
| 9,839,762 B2 | 12/2017 | Berg et al. |
| 2005/0185398 A1 | 8/2005 | Scannell, Jr. |
| 2007/0207220 A1 | 9/2007 | Luedtke et al. |
| 2008/0223953 A1* | 9/2008 | Tomono ............... A61M 11/042 128/200.16 |
| 2010/0309434 A1 | 12/2010 | Van Schijndel et al. |
| 2010/0331607 A1 | 12/2010 | Pelgrim et al. |
| 2011/0015500 A1 | 1/2011 | Wu |
| 2011/0160619 A1 | 6/2011 | Gabara |
| 2013/0317414 A1 | 11/2013 | Shalon et al. |
| 2013/0324788 A1* | 12/2013 | Holley ................. A61M 16/06 128/202.16 |
| 2015/0086951 A1* | 3/2015 | Bulut ..................... G09B 19/00 434/236 |
| 2015/0190607 A1 | 7/2015 | Sugio et al. |
| 2015/0290419 A1 | 10/2015 | Kare et al. |
| 2015/0297330 A1 | 10/2015 | Ficacci |
| 2015/0313496 A1* | 11/2015 | Connor ................. A61B 5/369 600/301 |
| 2017/0049597 A1 | 2/2017 | Manne |
| 2017/0053068 A1 | 2/2017 | Pillai et al. |
| 2017/0312476 A1 | 11/2017 | Woo |
| 2017/0319816 A1 | 11/2017 | Sokol et al. |
| 2017/0361133 A1 | 12/2017 | Yu et al. |
| 2018/0050171 A1 | 2/2018 | Tabert et al. |
| 2018/0125256 A1 | 5/2018 | Tsern et al. |
| 2020/0129727 A1 | 4/2020 | Lazarovich |

OTHER PUBLICATIONS

Tanaka et al., "Statistical Features of Hypnagogic EEC Measured by a New Scoring System", 1976; Sleep, 19(9): 731-738.

* cited by examiner

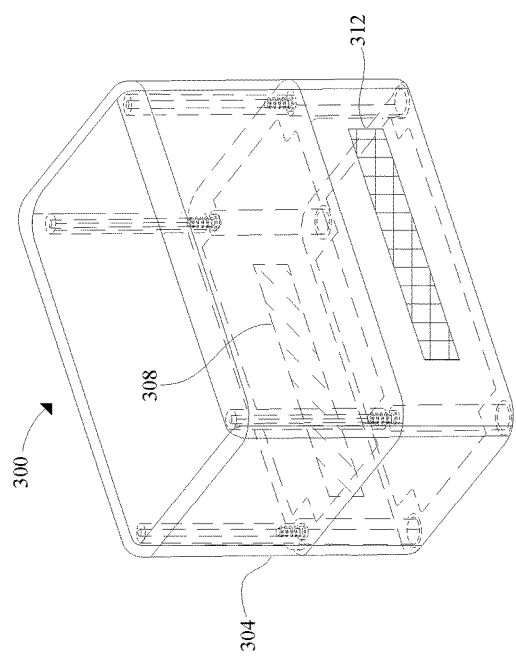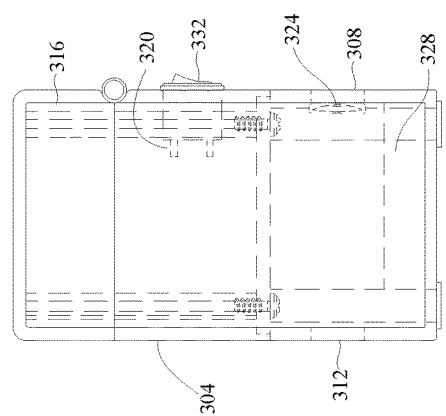
FIG. 3A
FIG. 3B

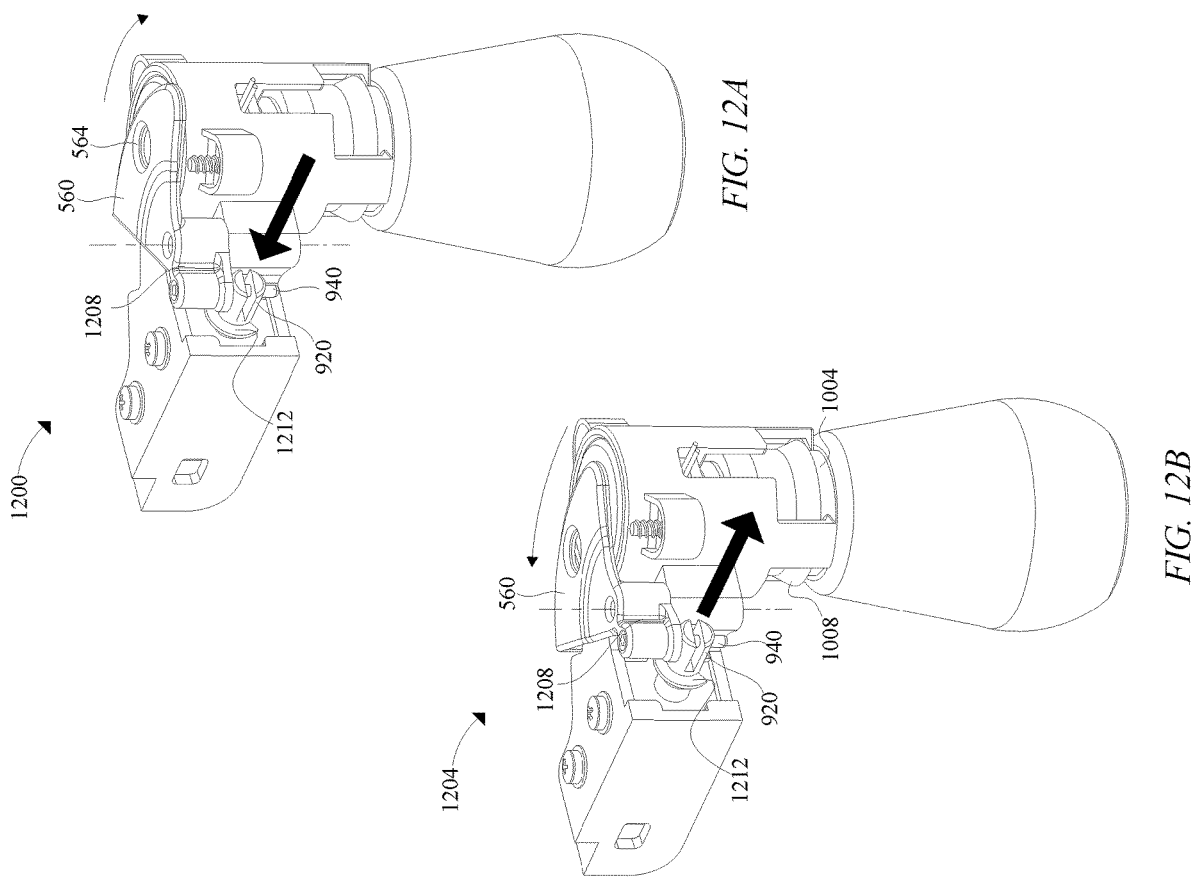

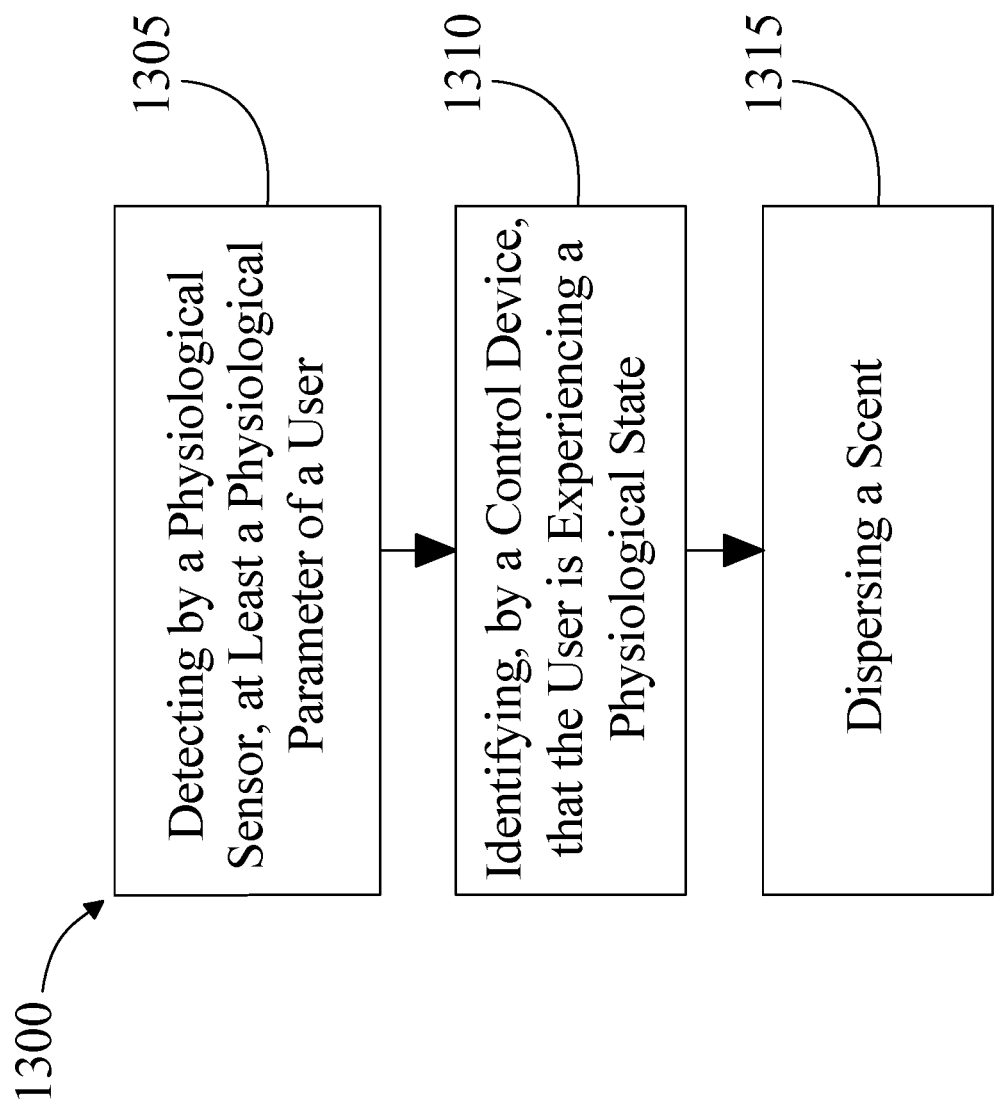

METHOD OF SYSTEM FOR INDUCING A PAVLOVIAN CONDITIONED ASSOCIATION OF AN AROMA WITH A STATE OF SATIATION

CROSS-REFERENCE TO RELATED APPLICATIONS

This application is a continuation-in-part of Non-provisional application Ser. No. 16/687,738 filed on Nov. 19, 2019 and issued as U.S. Pat. No. 10,842,433 on Nov. 24, 2020, and entitled "METHODS AND SYSTEMS USING CONDITIONING FOR PAIN MINIMIZATION," the entirety of which is incorporated herein by reference. This application claims the benefit of priority of U.S. Provisional Patent Application Ser. No. 62/798,659, filed on Jan. 30, 2019, and titled "METHODS AND SYSTEMS OF A PAVLOVIAN PAIN-FREE STATE," which is incorporated by reference herein in its entirety.

FIELD OF THE INVENTION

The present invention generally relates to the field of fluid handling and dispensing. In particular, the present invention is directed to methods and systems for inducing a Pavlovian conditioned association of an aroma with a state of satiation.

BACKGROUND

Successful weight management strategies must determine individual preferences for health, diet, exercise, lifestyle, and the like, for strategies to be effective. Doing so is oftentimes difficult in tailoring the strategy since satiation strategies are oftentimes not directed at solving the issues that contribute to an individual's driving motivations for weight gain.

SUMMARY OF THE DISCLOSURE

In an aspect, a system for inducing a Pavlovian conditioned association of an aroma with a state of satiation includes at least a physiological sensor, wherein the at least a physiological sensor is configured to detect at least a physiological parameter of a user, and to transmit a detection signal, a control device configured to receive the detection signal from the at least a physiological sensor, wherein the control device is further configured to ascertain that the user is experiencing a physiological state associated with satiation, and to transmit the detection signal to an automatically activated scent diffuser, thereby conditioning the user to associate said scent with satiation, and an automatically activated scent diffuser, wherein the scent diffuser is configured to automatically activate upon receiving the detection signal, wherein automatically activating further comprises diffusing a scent in response to the detection signal.

In another aspect, a method of inducing a Pavlovian conditioned association of an aroma with a state of satiation includes detecting, by a physiological sensor, at least a physiological parameter of a user, identifying, by a control device, that the user is experiencing a physiological state associated with satiation, and dispensing a scent, by an automatically activated scent diffuser, as a function of the user experiencing the physiological state associated with satiation.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 3A-3B is a diagrammatic representation illustrating a perspective view of an exemplary embodiment of an automatically activated scent diffuser;

FIGS. 12A-12B is a schematic representation of an exemplary embodiment of a first, bottle-open and bottle-closed configuration;

FIG. 13 is a flow diagram illustrating an exemplary method for conditional satiation;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for inducing a Pavlovian conditioned association with an aroma. Pavlovian conditioning may be developed between physiological patterns corresponding to, for instance, satiation, wherein identified behaviors that contribute to weight gain, such as overeating, can be stopped by the user by supplying an aroma using a device that supplies aromas. Aromas may be associated with moments of clarity to rebuff a behavior associated with weight gain, and reinforce behaviors supporting satiation. Moments of clarity may be detected using physiological sensors that carefully monitor aspects of user physiology associated with behaviors contributing to weight. Sensors may electronically activate the automatic scent diffusion device during particular moments to reinforce behaviors that support satiation and/or rebuff behaviors that contribute to weight gain. Once the mental association has been created between the aroma and the behavior, one can trigger the association by manually releasing the same scent; likewise one may experience the pleasure associated with a favorable aroma when participating in the behavior without the use of an aroma. Aroma diffusion may be performed by manual release using a manually actuated control device connected to the scent diffuser. Users may expect that experiencing the stimulus in the form of an aroma will be accompanied with a conditioned response that supports satiation strategies.

In an exemplary embodiment, after creation of the mental association, a kit including a user-activated scent diffuser device may then be provided to and used by the user (for example at home, while at work, during a workout, etc.) to assist in satiation strategies. Since the mental association has already been created, and automatic sensing may no longer be necessary. A kit including a user-activated scent diffuser need not communicate with sensors or other equipment to work. The user may be able to use the user-activated scent diffuser under any circumstances in which the user experiences challenges to maintaining a satiation strategy. Alternatively or additionally, a user-activated scent diffuser may be the same device as the automatically activated scent diffuser, wherein the automatically activated scent diffuser includes a user activation control so that the user may activate the scent diffuser, preprogram the scent diffuser to activate at predetermined times, or under any other user-controlled pattern.

Figure 1:
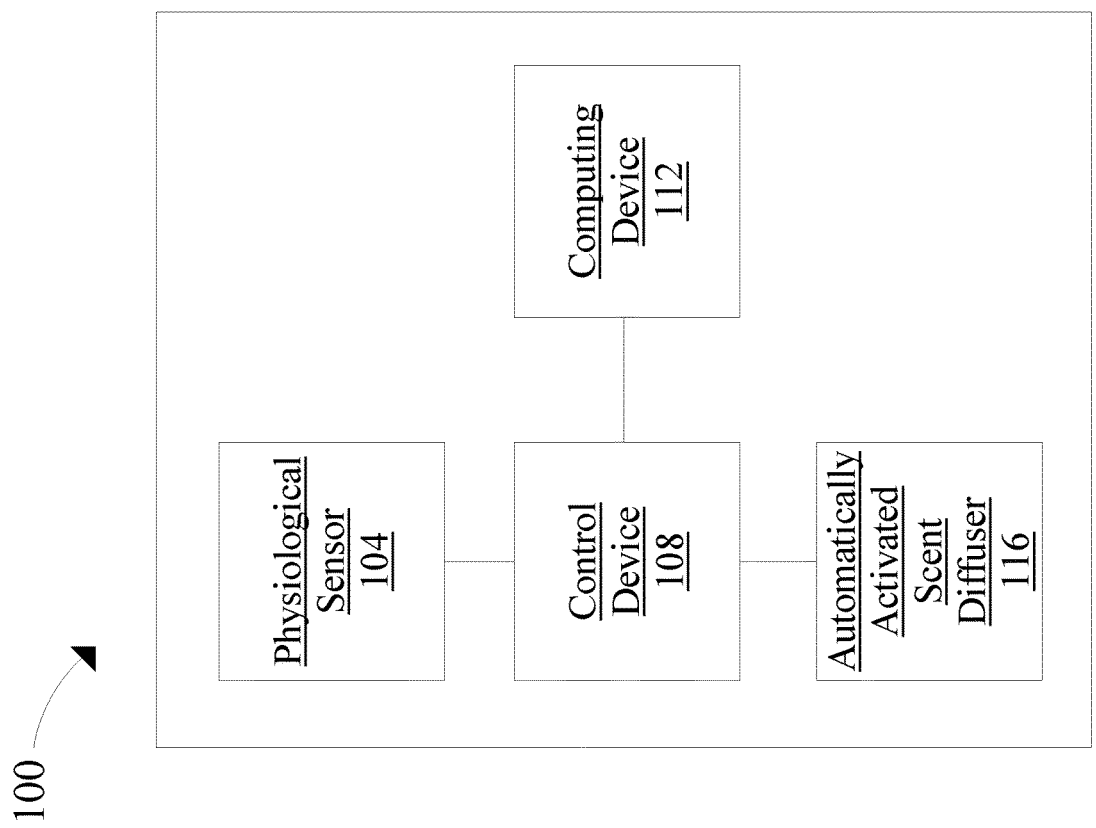
FIG. 1 is a block diagram illustrating an exemplary embodiment of a system for conditioning for satiation.

Referring now to FIG. 1, an exemplary embodiment of a system 100 for inducing a Pavlovian conditioned association of an aroma with a state of satiation is illustrated. As used in this disclosure, "satiation," is a condition defined as a state of inclination to noneating, characterized by an absence of hunger, which follows at or near the end of eating and arises from the consequences of food ingestion; satiation may include a psychological and physiological response to feeling "full". Satiation may be felt after an individual eats a meal until feeling satisfied and no longer hungry, and thus satiation may be reached by consuming an adequate amount of food in a specific period of time. Satiation may be marked by several emotional, psychological, digestive, and physiological patterns that can be recognized by questionnaire data pertaining to a user, as well as physiological sensor parameters. Achieving a feeling of satiation may be referred to as a behavior associated with weight reduction, as used herein. As used in this disclosure, "weight reduction" is weight loss, body mass index (BMI) improvement aimed at reducing body weight targeted at body fat, such as visceral body fat. "Weight reduction" herein may refer to improvement of lean body mass content, including increasing muscle mass and muscle tonus, through a strategy of reducing visceral body fat and/or improving musculature. Weight reduction is one of many body weight management strategies that may be suitable for use with the Pavlovian conditioning system described herein. Persons skilled in the art, upon review of the present disclosure in its entirety, will appreciate that the Pavlovian association of a scent with a state of weight reduction may be applied to many weight management and body composition strategies.

Continuing in reference to FIG. 1, system 100 includes at least a physiological sensor 104, wherein the at least a physiological sensor 104 is configured to detect at least a physiological parameter of a user. At least a physiological sensor 104 may be any device or component that measures a physiological parameter of a user and generates an electrical signal as a function of the measurement. At least a physiological parameter may include any information that may be sensed from a user's body, including for instance and without limitation any electrical, chemical, optical, auditory, olfactory, kinetic, or other information; at least a physiological parameter may include, for instance and without limitation, galvanic skin response or skin conductance response, pulse rate, respiration rate, blood flow, heartbeat signatures, electrolyte type and/or concentration, blood metabolite levels or ratios, blood pH level, position and/or balance, body strain, neurological functioning, neurological activity, blood pressure, bioimpedance, hydration, auscultatory information, body temperature, facial emotions, eye muscle movement, body movement, blood volume, inhaled and/or exhaled respiratory volume, exhaled breath physical and/or chemical composition, reflex response sleepiness, response to external stimuli, swallowing volume, swallowing rate, head position or tilt, internal body sounds, functional near-infrared spectroscopy signals, snoring, and/or other physiological information. Various non-limiting examples of such parameters are described in further detail in this disclosure regarding exemplary categories and/or embodiments of at least a physiological sensor 104.

Continuing in reference to FIG. 1, at least a physiological sensor 104 may include, without limitation, at least an electrophysiologic sensor, such as a sensor that detects at least an electrical, magnetic, or electromagnetic parameter, state, or reading regarding the body of the user. At least an electrophysiologic sensor may include an electrodynamic sensor device configured to sense an electrical activity of the heart, brain, and the like, of a subject. For example and without limitation, the electrodynamic sensor may be configured to sense a heart rate and/or heart rate variability (HRV) pattern using electrical activity of the heart, for instance using electrocardiography (ECG or EKG), or conductivity. Electrocardiography may include a process of recording electrical activity of a heart over a period of time using electrodes placed on the skin; electrodes may detect tiny electrical changes on the skin that arise from a heart muscle's electrophysiologic pattern of depolarizing during each heartbeat. An ECG may be used to measure rate and rhythm of heartbeats or other patterns relating to heartbeats, including without limitation heart rate variability patterns. Electrodes may be placed in contact with user's skin using any suitable means, including adhesion or incorporation in a wearable device such as a band of elastic material around user's torso, that places electrodes in contact with user's skin. In some embodiments, direct contact may not be necessary, and electrical functioning may be monitored capacitively, inductively, electromagnetically, or a combination of these approaches. In some embodiments, ECG or EKG may allow for continuous tracking and heart rate monitoring. In some embodiments, heart rate monitoring with ECG or EKG for example, may be performed on a user at rest such as when user is sitting or lying down, and/or when a user is exercising, such as walking on a treadmill at an incline. In an embodiment, at least an electrophysiologic sensor may include a Holter monitor. A Holter monitor may include wearable device such as a lanyard around a user's neck, that records a continuous ECG for a time. In an embodiment, a Holter monitor may include wires from electrodes that are placed on a user's chest, and which are connected to a battery-operated recording device worn around a user's neck, belt, or shoulder strap. In an embodiment, heart rate monitoring with ECG or EKG for example, may be performed using an event monitor.

Continuing in reference to FIG. 1, an event monitor may include a device, for instance and without limitation, like the above Holter monitor, but it may not record continuously as a Holter monitor would, but rather may record only at certain times of the day and/or for certain periods of time, and in some instances, recording may be prompted by a user, for instance and without limitation before, during, and after consuming a meal. An event monitor may contain a record button when a user may experience physiological states associated with eating, exercise, among other events, at which point sensors may become activate and start recording electrical activity. For example, in an embodiment, a user may wear an event monitor, and when user begins to consume a meal, user may record user's heart rate activity, among other parameters. When user experiences a state of satiety, user may also record user's heart rate activity, so that comparisons to electrical activity in each state can be examined. Persons having ordinary skill in the art, upon reviewing the entirety of this disclosure, will be aware of various ways in which physiological data may be collected, communicated, and analyzed consistently with the disclosure described herein.

With continued reference to FIG. 1, at least a physiological sensor may include a wearable device which includes an electrodynamic sensor device configured to sense an electrical activity of a subject. Wearable device may include for instance and without limitation, an electrophysiologic sensor worn around a user's neck, waistband, placed in a user's pocket, on a user's wrist and/or on a user's appendage. For example, electrophysiologic sensor may be contained within a wristwatch worn on a user's wrist, which contains electrodes that come into contact with the skin and are able to detect and record a user's heart rate activity and electrical impulses. In non-limiting illustrative examples, electrophysiologic sensor may include a Holter monitor worn on a lanyard around the neck, and/or worn around a user's belt that contains electrodes that come into contact with the skin. In further non-limiting illustrative examples, Monitor may be worn as a backpack on a user's back, which contains electrodes that come into contact with user's skin at various points along user's body. Electrophysiologic sensor may be contained, for instance and without limitation, within a ring worn on a user's finger, on a strap around the chest, or any other body placement pattern that may collect and transmit user physiological parameters.

With continued reference to FIG. 1, at least a physiological sensor may include a sensor that monitors neurological functioning. As a non-limiting example, electrophysiologic sensor may include one or more sensors that perform an electroencephalogram (EEG); EEG may involve detection of patterns, such as electrical impulses in the central nervous system, otherwise known as neural oscillations. Such electrical impulses may be associated with an individual's behavior, emotions, thoughts, motor activity, and the like, communicated between neurons within the central nervous system. EEG may be performed by detection of electrical patterns in neural activity using electrodes contacting user's cranium, such as electrodes placed along a forehead of user. Electrodes may be adhered to user or incorporated in a wearable device, such as without limitation an earpiece and/or headgear placing electrodes at cranial locations such as a forehead or temple. In some embodiments, direct contact may not be necessary, and neurological functioning can be monitored capacitively, inductively, electromagnetically, or a combination of these approaches. In some embodiments, neural activity may couple with low frequency acoustical sensors integrated into a head-mounted module, or the like. In non-limiting illustrative examples, monitoring may be performed continuously for a set duration of time, such as in a 24-48-hour continuous interval, such as when a user is monitored remotely from home. In further non-limiting illustrative examples, monitoring may be for a window of time such as, for example, a 3-hour period of time while a user is monitored under the supervision of a medical professional.

Continuing in reference to FIG. 1, at least an electrophysiologic sensor may include a sensor configured to perform an electrooculogram (EOG); EOG may be defined as an electrophysiologic measurement of eye motion. EOG may be collected using electrodes mounted at or near user's eyes, for instance through use of a mask or other wearable device that contacts the user's eyelids or rests nearby. EOG may be detected through contactless means such as capacitive, inductive, or electromagnetic detection. Alternatively or additionally, at least an electrophysiologic sensor may include electrodes or other sensors for monitoring an electromyogram (EMG) signal measuring electrical activity of muscles or muscular tissue of a user. At least an electrophysiologic sensor may include an electrodermal activity (EDA) sensor, also known as skin conductance, galvanic skin response (GSR) sensor, electrodermal response (EDR) sensor, or the like, which may measure continuous variation in electrical characteristics of skin. GSR sensors may include one or more sensors that detect changes in electrical activity resulting from changes in sweat gland activity. A signal may be sent through an electrode to the contact point with a user's skin whereby data is then gathered and transmitted to the GSR sensor. In an embodiment, increased sympathetic nervous system activity may be correlated with bodily indicators of arousal of the sympathetic nervous system such as increased heart rate, blood pressure, and sweating. In an embodiment, increased parasympathetic nervous system activity may be associated with bodily indicators of arousal of the parasympathetic nervous system such as decreased heart rate, blood pressure, and sweating. In an embodiment GSR response may be measured by placing two electrodes on a user's body. A low constant voltage may then be applied, whereby a voltage difference between the two electrodes may then be measured. Skin conductance may then be measured and reported. For example, electrodes may be placed on two fingers, both hands, and/or both feet.

Continuing in reference to FIG. 1, at least a physiological sensor 104 may include one or more sensors configured to detect facial expression. For instance and without limitation, one or more sensors may be configured to detect movement and expression of facial nerves and muscles that may indicate a user's sympathetic and parasympathetic response to a stimulus. At least a physiological sensor may include a facial electromyography which may track the activity of facial muscles with electrodes attached to the surface of a user's skin. In an embodiment, facial electromyography may detect and amplify electrical impulses generated by muscle fibers during contraction. Facial electromyography may place electrodes on a user's face at locations near major muscle groups, including locations near the left or right Corrugator Supercilia and the left or right Zygomaticus. Facial expressions detected by facial electromyography may be categorized by the Facial Action Coding System (FACS)

which represents a standardized classification system of facial expressions based on anatomic features. Expressions and anatomic features may provide insight into a user's emotional state, behavioral state, comfortability, and the like. For example, an image of a user, whose mouth corners are pulled upward, indicates that a user is smiling and thus not experiencing pain, excessive hunger, or other discomforts.

Continuing in reference to FIG. 1, at least a physiological sensor 104 may include one or more sensors configured to detect arterial or vascular data. For instance, and without limitation, at least a physiological sensor 104 may include a photoplethysmography (PPG) sensor, which may sense the body's rate of blood flow using a light-based technology whereby a light source is emitted through or at tissue containing blood vessels, and light reflected by or transmitted through the tissue is measured. At least a physiological sensor 104 may include an impedance plethysmograph for measuring changes in volume within an organ or body (usually resulting from fluctuations in the amount of blood or air it contains). For example, an impedance plethysmograph to monitor blood pressure in real-time. At least a physiological sensor 104 may include a sensor to detect pulse oximetry, where pulse oximetry is a standard noninvasive technique of estimating blood gas levels. Pulse oximeters typically employ two or more optical wavelengths to estimate the ratio of oxygenated to deoxygenated blood. Similarly, various types of hemoglobin, such as methemoglobin and carboxyhemoglobin may be differentiated by measuring and comparing the optical absorption at key red and near-infrared wavelengths. Additional wavelengths may be incorporated and/or replace conventional wavelengths. For example, by adding additional visible and infrared wavelengths, myoglobin, methemoglobin, carboxyhemoglobin, bilirubin, and blood urea nitrogen (BUN) may be estimated and/or monitored in real-time in addition to the conventional pulse oximetry. At least a physiological sensor 104 consisting of a pulse oximeter may include a sensor, attached to a user's finger, which measures blood saturation directly on contact with the skin. In an embodiment, the pulse oximeter may include a portable, battery-operated device that can be used remotely by a user, without direct medical supervision.

Continuing in reference to FIG. 1, at least a physiological sensor 104 may monitor blood pressure, using, as a non-limiting example, a digital blood pressure monitor; digital blood pressure monitor may include actuators and sonic and pressure transducers placed on the skin, and may measure systolic and/or diastolic pressure, for instance and without limitation, by monitoring a pressure at which a "Korotkoff sound" is first heard (systolic), then disappears (diastolic). Such a technique may also be used to monitor intra-cranial pressure and other internal pressures, and the like. Blood pressure may also be measured by comparing the time between pulses at different regions of the body. At least a physiological sensor 104 may alternatively or additionally include pyroelectric sensor for monitoring heart rate, heart rate variability patterns, pulse, pulse variability patterns, and the like.

Continuing in reference to FIG. 1, at least a physiological sensor 104 may include a body temperature sensor, which may be any sensor that acquires a temperature of user's body or a portion thereof. Temperature sensor may include, without limitation one or more infrared sensors, which may be composed of thermoelectric/pyroelectric materials or semiconductor devices, such as photodiodes or photoconductors, thermistors, thermocouples, or any other elements or components used in digital and/or electric thermometers or other temperature sensors. Temperature sensor may detect a skin temperature at one or more locations on user's body. Temperature sensor may contact user, or may detect user temperature remotely, for instance by capturing infrared radiation. Temperature sensor may also be a conventional thermometer, such as an oral thermometer, that may sample a user's temperature at specific times.

Continuing in reference to FIG. 1, at least a physiological sensor 104 may include at least a motion sensor. At least a motion sensor may include at least a gyroscope, which may detect orientation changes of the at least a gyroscope; multiple gyroscopes may detect orientation changes with respect to multiple axes, such as three gyroscopes to detect orientation changes with respect to three axes of rotation, or the like. At least a motion sensor may include at least an accelerometer, such as one or more microelectromechanical systems (MEMS) devices. An accelerometer may measure acceleration or position in two or more axes; alternatively or additionally, at least an accelerometer may include a plurality of accelerometers to detect acceleration with respect to a plurality of axes, such as without limitation three accelerometers that detect motion with regard to three dimensional axes. At least a motion sensor may include an inertial measurement unit (IMU), which may include multiple types of motion sensors in a single chip or system. At least a motion sensor may be mounted to one or more parts of user's body to detect motion thereof. Changes in patterns in user motion may indicate a transition by user from a pain-state to a pain-free state; for instance, a transition from a pain-state to a pain-free state may be accompanied by decrease in or cessation of movement by user, and/or by an increased regularity of chest movements indicating regular breathing.

As a further non-limiting example, and still referring to FIG. 1, at least a physiological sensor 104 may include at least an audiovisual capture device, such as a camera. At least a camera may be any electronic device capable of capturing light, whether in visible or non-visible spectra, and transmitting an electrical signal based on the detection. At least a camera may, as a non-limiting example, capture an eye area of user may be captured by a camera to determine whether or not an eye movement occurs based on the analysis of the captured images; when the eye rapidly moves such as for example when a user enters REM sleep, user may be satiated, hungry, in pain, among other states. Camera may detect body movement of user, which may be used similarly to body movements detected by at least a motion sensor; camera may, for instance, capture a sequence of images of user's body and compare images of the sequence of images to determine whether user has moved user's body, and if so, how frequently or to what extent. Camera may detect mobility of user, such as for example when a user is first mobile after surgery. Camera may detect if a user is immobile, such as for example when a user is lying in a bed in a recovery room immediately after undergoing surgery or is immobile because a user is intubated and receiving treatment in the intensive care unit.

Continuing to refer to FIG. 1, at least a physiological sensor 104 may include at least an acoustic sensor, such as a microphone or the like. At least an acoustic sensor may detect and/or monitor breathing characteristics of user, for instance via auscultatory signal extraction. In an embodiment, an acoustic sensor may be used to sense sounds associated with breathing. Signal processing algorithms may then be used to extract breathing sounds from other sounds and noise, for instance using digital signal filtering or noise elimination processes. This information may be used, as a non-limiting example, to measure and/or track intensity, volume, and speed of breathing, which may in turn be used to determine a user's state of wakefulness, pain-state, or pain-free state. Alternatively or additionally, at least a physiological sensor 104 may monitor breathing, using pressure transducers. For instance and without limitation, changes in pressure inside or near the ear associated with breathing may be measured directly and, through signal processing, translated into a breathing monitor. Similarly, optical reflection sensors may be used to monitor pressure by monitoring physical changes in the skin or tissues in response to breathing. For monitoring the physical changes of the tympanic membrane in response to breathing, and hence ascertaining breathing rate, an optical signal extraction approach may be employed. As a further non-limiting example, microphones positioned correctly near a sleep surface can sometimes pick up and detect a heartbeat and respiration. Microphones may also hear user's complaints that user is unable to sleep because of pain-state, and/or hear that user was silent because user was in a pain-free state and thus was able to sleep uninterruptedly. Microphones may also be utilized to detect when a user is eating, for instance detecting noise from chewing, drinking, and the like, wherein sound may be detected for instance and without limitation from within the ear canal, wherein the noise can be isolated from other auditory events.

Still referring to FIG. 1, at least a physiological sensor 104 is configured to detect at least a physiological parameter of a user and transmit a detection signal. A detection signal may be used herein to refer to any signal of physiological detection from a physiological sensor. Detection signal may be an activation signal of the automatically activated scent diffuser, depending on the nature of the physiological detection, as described in further detail below. Detection signal may be transmitted via wired connection to one or more other elements of system 100 as described below; for instance, and without limitation, at least a physiological sensor 104 may be incorporated in a single electronic device, or mounted on a single chip, with one or other additional components of system 100. Alternatively or additionally, detection signal may be transmitted to one or more components of system 100 wirelessly. For instance, and without limitation, at least a physiological sensor 104 may include one or more wireless transceivers, which may communicate according to protocols such as Bluetooth, Wi-Fi, and/or any other suitable wireless communication method and may be configured to transmit information wirelessly one or more other components of system 100.

Continuing in reference to FIG. 1, physiological sensor 104 may transmit a detection signal to a control device 108. Control device 108 communicating with the physiological sensor 104 may include a computing device, processor, of the like, as described in further detail below. Control device 108 may analyze a physiological sensor 104 signal, wherein analyze may be calibration using input signals during a state of non-activity, normal state, abnormal state, eating, exercising, and the like. Analysis performed by a control device 108 may include training, wherein the control device 108 may use a training epoch, for instance with a neural network or similar machine-learning algorithm, for instance where the control device 108 may train with physiological signal to determine user behaviors, states, movements, activities, and the like, by delineating noise from signal. In a non-limiting illustrative example, control device 108 may train with physiological sensor 104 data during times of a certain behavior and times of non-behavior activity to better determine when the Automatically activated scent diffuser 116 may actuate.

Still referring to FIG. 1, control device 108 may include any digital and/or analog control circuit. For instance and without limitation, control device 108 may include a logic circuit incorporating one or more logic gates. Control device 108 may include a microprocessor, microcontroller, or any computing device as described below. As a non-limiting example, control device 108 may include a mobile computing device such as a "smartphone", laptop, computer, or the like. Control device 108 may be communicatively connected to automatically activated scent diffuser 108, at least a physiological sensor 104, and/or user display, where "communicative connection" is defined as a relationship between two or more devices or components whereby the two or more devices or components are capable of sending and/or receiving electrical or wireless signals to and/or from each other; for instance, where automatically activated scent diffuser 108 includes a transceiver or other wireless communication device, control device 108 may include a transceiver or other wireless communication device capable of communication with the transceiver or other wireless communication device of the automatically activated scent diffuser 108. Alternatively or additionally, control device 108 may be connected to automatically activated scent diffuser 108 and/or other components via a wired connection, by way of one or more intermediate devices, or by incorporation in the same component, chip, or circuit as automatically activated scent diffuser 108.

Further referring to FIG. 1, control device 108 may be designed and/or configured to perform any method, method step, or sequence of method steps in any embodiment described in this disclosure, in any order and with any degree of repetition. For instance, control device 108 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Control device 108 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing to refer to FIG. 1, control device 108 communicating with the physiological sensor 104 may include a computing device 112, wherein the computing device 112 may be configured to analyze the physiological sensor 104 signal. Analysis of physiological sensor 104 data may be performed, for instance and without limitation, by training a machine-learning model with training data; the training data may include a plurality of data entries, each of which may include a detection signal from a plurality of physiological sensors 104, which may be correlated with a state of weight reduction and/or satiation, for instance and without limitation as described in further detail below.

Still referring to FIG. 1, "training data," as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and with continued reference to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

Further referring to FIG. 1, a "machine learning process," as used in this disclosure, is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language."

Still referring to FIG. 1, control device 104 and/or computing device 108 may be designed and configured to create a machine-learning model using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perception model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Still referring to FIG. 1, machine-learning algorithms may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs as described above as inputs, outputs as described above as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

Continuing in reference to FIG. 1, supervised machine-learning processes may include classification algorithms, defined as processes whereby a computing device derives, from training data, a model for sorting inputs into categories or bins of data. Classification may be performed using, without limitation, linear classifiers such as without limitation logistic regression and/or naive Bayes classifiers, nearest neighbor classifiers, support vector machines, decision trees, boosted trees, random forest classifiers, and/or neural network-based classifiers.

Still referring to FIG. 1, machine learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 1, machine-learning processes as described in this disclosure may be used to generate machine-learning models. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Further referring to FIG. 1, training data may include physiological signals during different periods, such as periods of eating and periods of non-eating, wherein a physiological background may be captured for periods of non-eating, and a that signal may be used to calibrate a 'zero point' of the physiological parameters and the 'excited state' may be the increase and/or decrease in physiological parameters captured by the sensors during the period of eating. Computing device 108 may take training data corresponding to physiological sensor data during a variety of actions, events, or the like, and train a machine-learning model for a variety of physiological parameters related to weight reduction behaviors. The machine-learning model may then sample physiological sensor 104 input data in real-time and generate an output that is a determination about whether a user is engaging in behavior that is productive for weight reduction and/or counter-productive to weight reduction. Computing device 104 with such machine-learning models may then quickly analyze incoming physiological sensor 104 input data to determine 'moments of clarity'. As used in this disclosure, "moment of clarity," is any moment when a user is engaging in a behavior, action, effort, task, or the like, carried out by the user that may be identified by physiological sensors that is associated with weight reduction, when the user would otherwise engage in behavior that contributes to weight gain. A moment of clarity may be a period of decision making for a user after which a user may engage in a behavior that is productive towards weight reduction. Computing device 104 may determine such moments of clarity by analyzing physiological sensor 104 detection signals transmitted via a control device 108. Alternatively or additionally, computing device 104 may determine moments of clarity from user questionnaire data, user input data, user caloric tracking data, user exercise data, and the like, that is user-originated data that described behaviors productive toward weight reduction, wherein the physiological sensor data may be further analyzed with indications of these events. Training data correlating physiological sensor data to moments of clarity may be generated using such data and used to train a machine-learning model and/or process to detect moments of clarity as a function of physiological sensor detection signals. Such training data may be used, without limitation, to train a machine-learning model that identifies moments of clarity given inputs of physiological sensor data indicative thereof; such a machine-learning model may be trained using any suitable machine-learning algorithm, including without limitation a machine-learning algorithm as described above.

With continued reference to FIG. 1, training data used for training a machine-learning model may include clinical, scientific, and/or any other research data that relates physiological parameters, as described above, with behaviors, emotions, physiological, and/or physiological states associated with behaviors regarding weight gain, weight reduction, satiation, and/or motivation for exercising. A machine-learning model may be generated to detect such a such a state based on one or more detection signals as described in this disclosure. For instance and without limitation, clinical data that relates wearable bioimpedance of extremities, oxygenation sensors data, heart rate, systolic and diastolic blood pressures, breathing patterns, inspiratory muscle activation data, brain signaling patterns, blood chemistry data, gastric distention, among other clinical and physiological data may be correlated periods of satiation, readiness to engage in physical activity, or other physiological states that are and/or are correlated with states of weight reduction. Training data may be used, without limitation, to train a machine-learning model that identifies moments of clarity given inputs of physiological sensor data indicative thereof; such a machine-learning model may be trained using any suitable machine-learning algorithm, including without limitation a machine-learning algorithm as described above.

With continued reference to FIG. 1, training data for training a machine-learning model may include data, such as described above, to output a model that contains a type of automatic programming wherein data can be input into the model, and the qualitative and/or quantitative relationships contained in the model will generate an output that system 100 may use to guide dispensing an aroma and/or may inform a user when to dispense a scent. Computing device 108 may accept an input of detection signals from at least a sensor, as described above, and use the input as training data for a machine-learning model. Once a machine-learning model has been trained, the model may be used for satiation detection with subsequent detection signal input and for subsequent steps described herein. Alternatively or additionally, heuristics present in the model may be presented via a user device, such as a "smartphone", laptop, tablet, or the like, that may inform a user on when to most effectively diffuse a scent for subsequent uses. Such training data may be used, without limitation, to train a machine-learning model that identifies satiation given inputs of physiological sensor data indicative thereof; such a machine-learning model may be trained using any suitable machine-learning algorithm, including without limitation a machine-learning algorithm as described above.

With continued reference to FIG. 1, machine-learning models may be used generate outputs which represent further training data and/or inputs for downstream machine-learning processes. For instance and without limitation, broad spectrum biomarkers and narrow spectrum biomarkers associated and/or correlated with states of weight reduction, such as without limitation states of satiation and/or states of motivation to engage in exercise, may be correlated with such states in training data. A machine-learning model may be generated to output such states based on either kind of biomarker. As used in this disclosure, "broad spectrum biomarkers" are biomarkers that falling within in a comprehensive range of biomarkers that may be measured in a clinical setting. Broad spectrum biomarkers may include biomarkers that may be obtained through invasive means outside of physiological sensors including blood tests, x-rays, biopsies, and the like. A "narrow spectrum biomarker," as used in this disclosure, is a biomarker that is detectable using sensors deployed in a home setting, such as wearables or the like, such as non-invasive pulse and/or heartrate measurement devices, galvanic skin response detectors, pulse oximeters, volatile organic compound (VOC) detectors, imaging devices such as cameras, image analysis tools, breath and/or eye-tracking devices, or the like. In non-limiting illustrative examples, a machine-learning process may use training data associating broad-spectrum biomarkers to states of weight loss to train a machine-learning model that can input broad spectrum biomarkers and output state of weight loss for all users and/or for a specific user; machine-learning models may, in a non-limiting example, be trained first with training data relating to all users, and then further trained with training data specific to a particular user. In non-limiting illustrative examples, a machine-learning process may use training data, correlating broad spectrum biomarkers with states of satiation to train a machine-learning model that inputs broad spectrum biomarkers and outputs a state of satiation for all users and/or a single user; machine-learning models may, in a non-limiting example, be trained first with training data relating to all users, and then further trained with training data specific to a particular user. In non-limiting illustrative examples, a machine-learning process may use training data correlating narrow spectrum biomarkers to states of weight loss to train a machine-learning model that inputs narrow spectrum biomarkers and outputs a state of weight loss and/or satiation for all users and/or a particular user; machine-learning models may, in a non-limiting example, be trained first with training data relating to all users, and then further trained with training data specific to a particular user. In non-limiting illustrative examples, a machine-learning process may use training data, correlating narrow spectrum biomarkers with broad spectrum biomarkers for all users and/or a specific user; machine-learning models may, in a non-limiting example, be trained first with training data relating to all users, and then further trained with training data specific to a particular user. In non-limiting illustrative examples, a machine-learning process may use training data correlating narrow spectrum biomarkers to broad spectrum biomarkers to train a machine-learning process that inputs narrow-spectrum biomarkers and outputs corresponding broad-spectrum biomarkers for all users and/or a particular user; machine-learning models may, in a non-limiting example, be trained first with training data relating to all users, and then further trained with training data specific to a particular user. Any training data as described above may include entries generated by machine-learning models and/or processes as described above. Any inputs to a machine-learning model may be generate by other machine-learning models and/or processes, and/or received, generated, and/or retrieved in any manner described in this disclosure.

Furthermore, still referring to FIG. 1, computing device 108 and/or machine-learning process may retrain models based on user feedback, for instance and without limitation, when the aroma did or did not help with weight reduction and/or inciting a feeling of satiation, and the like. For instance and without limitation, user may enter feedback using a graphical user interface, form-entry, or the like, that may be associated with an instance of aroma use, detected data, or the like to which the user is referring, and the association is used to modify training data and/or add to training data, which may then be used in turn to retrain one or more machine-learning models as described in this disclosure. This process may be performed for all users based on a repository of data, online-retrievable data, database repository of data, and the like; alternatively or additionally, the process may be specific to a single user and iteratively improved as more data is generated. Such training data may be used, without limitation, to retrain a machine-learning model, such as without limitation any machine-learning model as described in this disclosure; such a machine-learning model may be trained using any suitable machine-learning algorithm, including without limitation a machine-learning algorithm as described above. Persons skilled in the art, upon review of this disclosure in its entirety, will be aware of the various ways in which user feedback may be input into computing device to be used to retrain machine-learning models.

Continuing in reference to FIG. 1, in non-limiting illustrative examples, a machine-learning model may be trained with physiological sensor data that relates to several distinct states such as: 1) when a user is asleep, 2) when a user is awake and not hungry, 3) when a user is awake and hungry, and 4) when a user is awake and satiated, to achieve precise and accurate baseline thresholds that adequately gauge how a user feels throughout the day to determine when a user may be looking to consume a meal and when a user has quelled food cravings—by eating or otherwise. In such an example, these four machine-learning models may be used by a machine-learning process to learn and more quickly determine if incoming detection signals from physiological sensors 104 indicates that a user is experiencing hunger and/or satiation. Further, the machine-learning process may track when aroma diffusion occurs and determine if the detection signals show a user was in a state of hunger prior to scent diffusion and if after an aroma is diffused the detection signals show a user feels more satiated without the use of food. Such a process may inform system 100 if a Pavlovian conditioned association between the aroma and, for instance, satiation has been achieved. Such training data may be used, without limitation, to train and/or retrain a machine-learning model that as described above; such a machine-learning model may be trained using any suitable machine-learning algorithm, including without limitation a machine-learning algorithm as described above.

Continuing in reference to FIG. 1, alternatively or additionally, computing device 104 may analyze input physiological sensor 104 detection signals transmitted via a control device 108 by using threshold values, or other binary assessments. Computing device 104 may have a predetermined threshold value, for instance and without limitation, percent heart rate increase, numerical value systolic and/or diastolic blood pressure increase, and the like, wherein computing device 104 analysis may be a determination of whether a user is above or below the threshold value. Computing device 104 may use a logic gate, microprocessor, among other components described herein, to send a detection signal to actuate the automatically activated scent diffuser when the analysis performed has indicated a state wherein a user should experience the aroma.

Continuing in reference to FIG. 1, automatically activated scent diffuser 116 activating upon receiving the detection signal may include determining by the control device 108 if a physiological sensor is detecting an event associated with weight reduction. Control device may determine by analysis of user physiological sensor data when a behavior associated with weight reduction is taking place. Control device 108 may receive a detection signal, analyze detection signal to determine if detection signal is related to an event associated with weight reduction, and relay the detection signal to the automatically activated scent diffuser 116 to activate, as described in further detail below. In such an event, the automatically activated scent diffuser 116 may recognize the signal to activate from the control device 108.

Continuing to refer to FIG. 1, system 100 includes an automatically activated scent diffuser 116, wherein the automatically activated scent diffuser 116 is configured to automatically activate upon receiving a detection signal, wherein automatically activating may include diffusing a scent in response to the detection signal. Automatically activated scent diffuser 116 may be any device that can selectively release a scent into the air, so that a user may smell the scent, including for instance and without limitation, instant action scent diffusers such as aerosolization sprayers, atomizers, vaporizers, foggers, aromatherapy diffusers, heating elements for essential oils, waxes, candles, and the like. Continuing in reference to FIG. 1, automatically activated scent diffuser 116 may include housing to house a fragrance container. Fragrance container may include a scent diffuser and/or a scent source, which may include a material that releases scent molecules into the air. Scent molecules may include any molecules that human olfactory receptors detect as having an aroma. Scent molecules may pass through air to a user's nose by diffusion. Scent molecules may have aromas recognizable to users; aromas may include aromas generally considered pleasant, such as the aromas of fruits, flowers, herbs, pine needles, or the like. Scent source may include a material containing one or more volatile materials that either have the desired aroma or carry molecules having the desired aroma in solution. Scent source may include one or more scent wafers, which may release scent upon exposure to air, for instance by evaporation of volatile materials contained within scent wafer. Scent source may include one or more scent liquids, such as perfumes, essential oils, or the like; scent liquids may be volatile, or contain volatile materials, causing diffusion through evaporation. Scent-diffusing material may include a gas.

Continuing in reference to FIG. 1, the scent source may be in any other suitable form, including a film, foam, wafer, or gel. The scent source may include a material that releases scent molecules under specific circumstances; for instance, the scent source may include a wafer, film, liquid ampule, or other material that releases scent only on exposure to heat, electric current, or the like. In non-limiting illustrative example, the scent source may contain a mixture or solution of volatile or scent-diffusing material with a substance that seals the scent-diffusing material at a first temperature, such as room temperature, but changes to release scent-diffusing material at a second temperature, which may be a higher temperature; substance may be waxy, may have a structure that encapsulates scent-diffusing material in small envelopes and/or capsules of material that will open or rupture upon exposure to heat, or may combine with scent-diffusing material via chemical bonds that release upon heat exposure. Alternatively or additionally, substance may be a material that encapsulates or maintains a chemical bond to scent-diffusing material until exposed to an electric current or field. In an embodiment, removal of a release stimulation may result in a cessation of diffusion of scent; for instance, where substance encapsulates scent-diffusing material until exposure to ultrasonic vibration, heat or electric currents and/or fields, cessation of heat, ultrasonic vibration, or electric currents and/or fields may cause substance to re-encapsulate scent-diffusing material. Similarly, chemical bonds that are separated by heat, ultrasonic vibration, and/or electric current and/or fields may reform upon cooling or cessation of the electric stimulus. Heat used to release scent-diffusing material may be applied using an electrical heating element, which may be controlled by a control device 108, microprocessor, microcontroller, or the like, as discussed in further detail below; electric current and/or field may be similarly provided electrically. Ultrasonic vibration may be applied using any electrically triggered sonic vibration generating component, such as without limitation piezoelectric vibrating components. The automatically activated scent diffuser may be located near user's head and/or nose, near olfactory sensory neurons located in the olfactory epithelium. Odorants may penetrate into the olfactory epithelium and mix with mucus which acts as a solvent for odor molecules, and is constantly replaced, for instance and without limitation, approximately every 10 minutes.

Continuing in reference to FIG. 1, scent-diffusing material may be contained in an enclosed container and selectively released. For instance, where scent-diffusing material includes a liquid or gel, scent-diffusing material may be contained in a cartridge, compartment, ampule, or bottle-like component that may be sealed until controlled release. Where scent-diffusing material includes a film, foam, or solid object such as a wafer, scent-diffusing material may be stored in a cartridge, wrapper, or compartment that may be selectively opened when scent diffusion is desired. A scent-diffusing gas may similarly be contained in a cartridge or compartment; scent-diffusing gas may be contained under pressure. Selective opening of enclosed container may include piercing a wrapper, opening a selectively closable aperture, or the like. Alternatively or additionally, liquid, gas, or gel may be released from one or more nozzles, such as spray nozzles for aerosolization; nozzles may be mechanically or electrically actuated in any suitable way, including forcing of scent-diffusing material through nozzles using a pump, impeller, or other pressure source, including pressurized cartridges. Nozzles may be actuated by opening a valve. An aperture of enclosed container may be opened by electrically controlled mechanical movement of a door or lid, for instance using an electric motor or linear actuator, a servo, or the like.

Continuing to view FIG. 1, automatically activated scent-diffuser may include one or more dispersal mechanisms. Where nozzles are used, dispersal may be aided in part by pressurized ejection from nozzles. Dispersal mechanisms may similarly include an ultrasonic nebulizer, an air-blowing component such as a fan, impeller, pump, or micropump, which causes airflow past scent-diffusing material, carrying it and resulting aromas to user's nose or speeding up diffusion to accomplish the same. Automatically activated scent diffuser 116 may be incorporated in a home heating, ventilation, and/or air-conditioning system, permitting air circulation of such a system to aid in dispersal or diffusion of scent molecules. In an embodiment, where automatically activated scent diffuser 116 includes a heater, the heater may cause air currents through convection, which may have a similar effect to air blowing component. One or more dispersal mechanisms may include additional or alternative components, such as a wick, which may draw scent-diffusing material using capillary action from a container or enclosure to exposure to open air, where evaporation may disperse scent-diffusing material or enclosure to exposure to open air, where evaporation may disperse scent-diffusing material. A dispersal mechanism may include an ultrasonic nebulizer atomizing the scent-diffusing material and dispersing it to open air. Automatically activated scent diffuser may be configured to stop diffusing scent upon reception of a deactivation signal.

Figure 2:
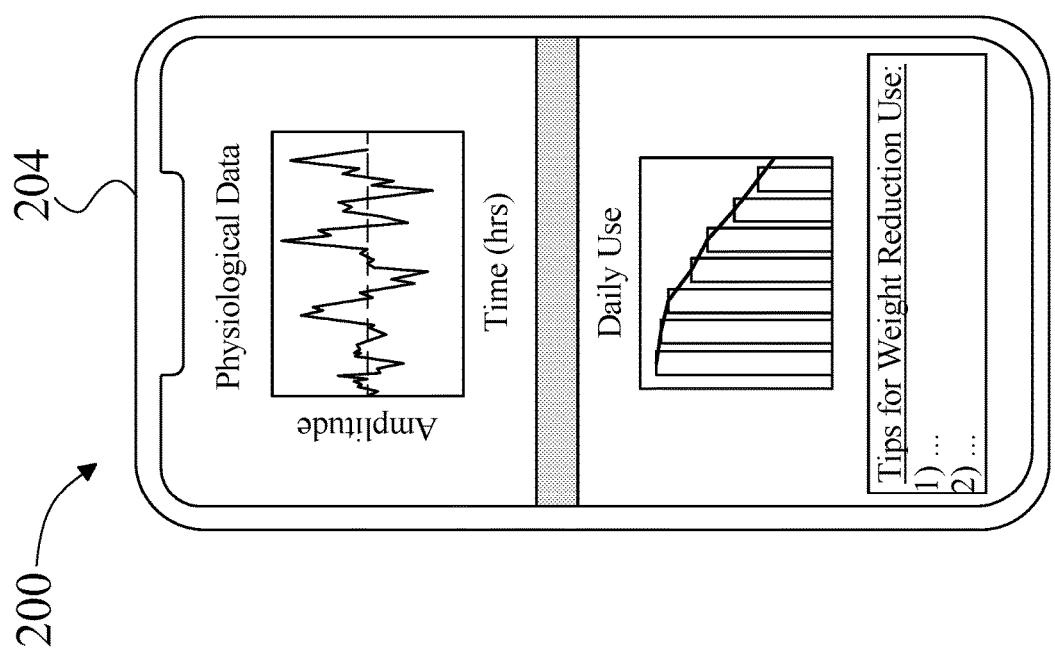
FIG. 2 is a diagrammatic representation of an exemplary embodiment of a user device.

Referring now to FIG. 2, a non-limiting exemplary embodiment 200 of the control device displaying to a user device is illustrated. User device may be the same as control device 112. As described above, control device 112 may comprise a computing device such as a "smartphone", laptop, or the like, wherein the computing device may have capability to display to a user via a graphical user interface (GUI), or the like. User device 204 may display graphics such as physiological sensor 104 data and analysis of said data, text such as instructions and metrics regarding use of the aroma diffuser, or the like. User device 204 may receive physiological sensor 104 data and/or the analysis of said data from computing device 112, wherein the data and/or analysis may inform a user on use of the user-activated scent diffuser provided in a kit, as described in further detail below. Persons skilled in the art, upon review of this disclosure in its entirety, will be aware of the various devices suitable for use as a user device, and will be aware of the ways in which graphics, text, and the like, may be displayed to a user via a user device.

Continuing in reference to FIG. 2, user device 204 is further configured to communicate with the automatically activated scent diffuser 116, wherein communication may include accepting user input command control. Automatically activated scent diffuser 116 may be the same as the user-activated scent diffuser, wherein the automatically activated scent diffuser 116 may recognize and accept user input commands. User input commands may be to activate the device, initiate scent diffusion, change user settings such as scent diffusion amount, duration, and the like. User input command control may be a command to switch between automatic activation and user-activated modes. User input command control may include designating the amounts and types of physiological sensors in use.

Continuing in reference to FIG. 2, the control device 112 may be further configured to transmit, to the automatically activated scent diffuser, a deactivation signal. Control device 112 may be configured to signal to activate automatically activated scent diffuser and have a predetermined scent diffuser duration, and send a second, deactivation signal to turn off the scent diffuser. The control device 112 may be further configured to activate upon user designated control, wherein activation by the user diffuses an identical scent diffused by the automatically activated scent diffuser. In non-limiting illustrative examples, control device may detect the presence of physiological sensors in communication with the device, wherein if physiological sensor data is input, the scent diffuser will operate in automatic mode; alternatively, if physiological sensors are not present, the control device may switch off automatic mode, allowing a user to manually control scent diffusion. Persons skilled in the art, upon review of this disclosure in its entirety, will be aware that the control device may allow designation of automatic activation of the scent diffuser or may switch to user-designated control.

Referring now to FIG. 3A, a non-limiting exemplary embodiment 300 of a perspective view of an automatically activated scent diffuser 116 is illustrated. Automatically activated scent diffuser 116 may have a housing 304, which may be in any suitable form, including without limitation a box form. Housing 304 may include an air intake 308, which may include or communicate with an aperture or selectively closable aperture of a compartment containing scent-diffusing material as described above. Housing 304 may include a diffusing vent 312, which may include a grid or other covering; diffusing vent 312 may include or communicate with an aperture or selectively closable aperture of a compartment containing scent-diffusing material, as described above.

Referring now to FIG. 3B, a side-view of a non-limiting exemplary embodiment of a perspective view of an automatically activated scent diffuser 116 is illustrated. Automatically activated scent diffuser 116 may prevent scent diffusion until receipt of a detection signal; for instance, where present, diffusing vent 312 and air intake 308 may be sealed initially, preventing scent dispersal. Upon an electronic detection signal, which may be received via any suitable means, including a signal to transceiver, automatically activated scent diffuser 116 may diffuse scent using any mechanisms, components, or combination thereof; for instance, and without limitation, where automatically activated scent diffuser 116 is as depicted. An aperture at diffusing vent 312 and/or air intake 308 may be opened and fan may be activated, causing airflow from air intake 308 to diffusing vent 312 to carry scent molecules out into the air, so that user may smell them. In an alternative or additional embodiment, automatically activated scent diffuser 116 may include a scent-diffusing module attached to or incorporated in a mobile device such as without limitation a smart phone. Housing 304 may include a manually activated opening 316, such as a hinged and/or latched lid, which may be used to open housing 304 and/or compartment containing scent-diffusing material; manually activated opening 316 may cause scent release when opened, be used to insert additional scent-diffusing material in automatically activated scent diffuser 116, or the like. Referring now to FIG. 3B, housing 304 may contain one or more components of automatically activated scent diffuser 116 as described above, including a communications module 320, such as a transceiver as described below, an electronic fan controller, an electric fan with a motor, a battery 328, and the like. Housing 300 may include a receptacle for a scent wafer. Housing 300 may include a power switch 332. It is important to note that in non-limiting exemplary embodiments, a scent diffuser may have an externally-exposed haptic control such as a joystick, lever, thumbwheel, switch 332, or the like, that may electromechanically control the fragrance diffusion, power the diffuser on, and the like. Those skilled in the art may appreciate, upon review of this disclosure in its entirety, that the diffuser described herein may be an automatically-activated scent diffuser controlled by a control device and/or computing device, and likewise the diffuser may be a manually-activated scent diffuser.

Figure 4:
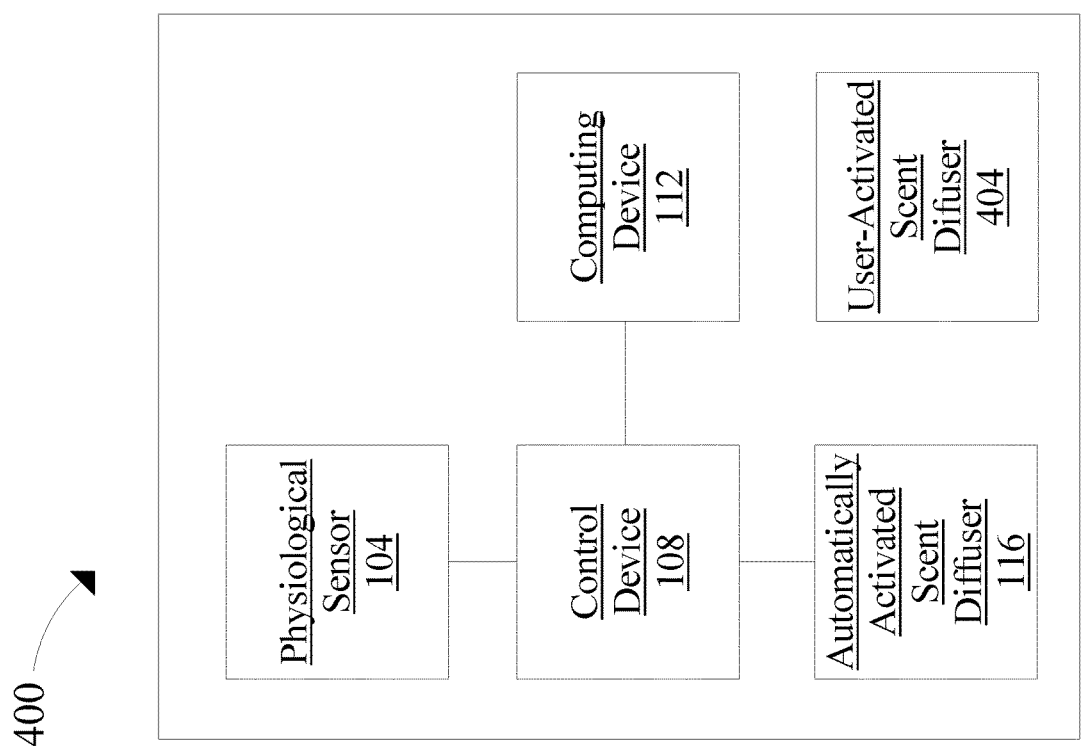
FIG. 4 is a block diagram illustrating an exemplary embodiment of a Pavlovian satiation kit.

Referring now to FIG. 4, an exemplary embodiment of a Pavlovian weight reduction kit 400 is illustrated. In an embodiment, kit 400 includes at least a physiological sensor 104 configured to detect at least a physiological parameter of a user and transmit a detection signal; this may be implemented using any components, devices, or processes described above in reference to FIG. 1-3B. Kit 400 includes an automatically activated scent diffuser 108 configured to receive an electronic detection signal and diffuse a scent as a function of the electronic detection signal; this may be implemented using any components, devices, or processes described above in reference to FIG. 1-3B. Kit 400 includes a control device 108 configured to receive the detection signal from the at least a physiological sensor 104, determine that the user is entering a state conducive to weight reduction, and transmit the electronic detection signal to the automatically activated scent diffuser 108. Control device 108 may be implemented and/or configured using any components, devices, or processes described above in reference to FIG. 1. Control device 108 may contain a computing device 104 used for analysis of physiological sensor 104 data.

Still referring to FIG. 4, kit 400 includes a user-activated scent diffuser 404 that diffuses the scent upon activation by a user. User-activated scent diffuser 404 may include a scent diffuser that diffuses scent upon activation by user; activation by user, as used herein, means direct activation by a voluntary act on the part of the user, in a process that does not include sensing physiological parameters or determining a user state. A user-activated scent diffuser 404 may be the same as an automatically activated scent diffuser, but with the automatic actuation function replaced with manual, user activation. For instance, user-activated scent diffuser 404 may include a switch that user turns on, causing release of scent, a manually activated opening 412, such as without limitation manually activated opening 412 as depicted above, which exposes scent-diffusing material, a heat source such as a candle or an electric heater that user can apply heat to substance containing scent-diffusing material, a vibration generating component to generate ultrasonic vibrations to release aroma, or the like. User-activated scent diffuser 404 may include a container, such as a portable container, that user may open and/or close manually; container may be constructed of any suitable material, including plastic, paper, metal, carbon fiber, ceramic, wood, or the like. Container may have a form of a box or wrapper that user opens to release scent. In a non-limiting example, user-activated scent diffuser 404 may include a container such as a box, wrapper, or sealed packet containing a scent wafer as described above, which user may activate by opening the container, and may deactivate by shutting or sealing the container. User-activated scent diffuser 404 may include any mechanism for scent diffusion and/or dispersal described above for automatically activated scent diffuser 108. User-activated scent diffuser 404 may be a separate device from automatically activated scent diffuser; alternatively, automatically activated scent diffuser 108 may function as user-activated scent diffuser by incorporation of one or more controls or features enabling user to activate scent diffusion. Scent diffused by user-activated scent diffuser 404 may be identical, or substantially identical, to scent diffused by automatically activated scent diffuser 108. User-activated scent diffuser 404 may include a scent-diffusing module attached to or incorporated in a mobile device such as without limitation a smart phone.

Figure 5:
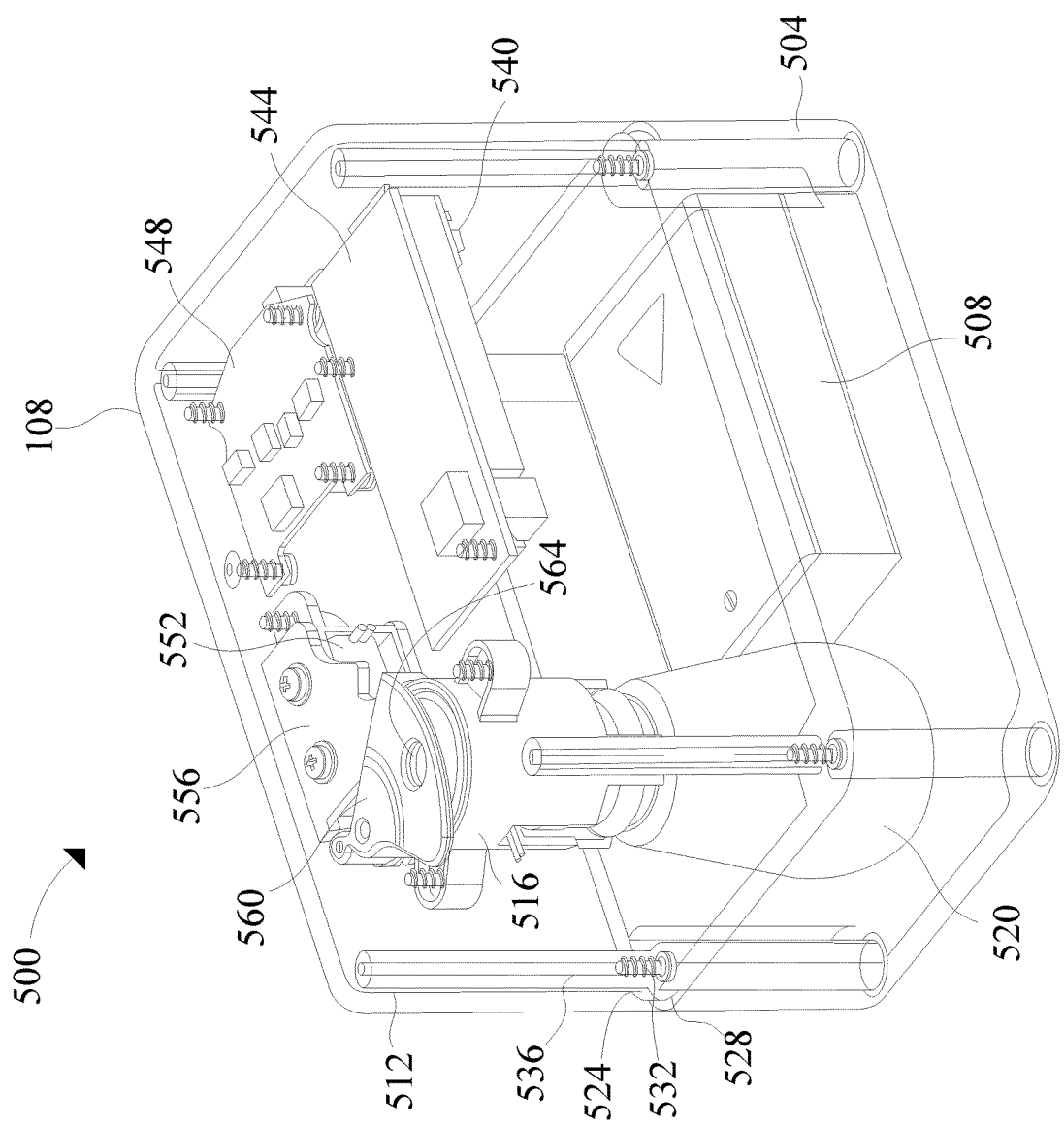
FIG. 5 is a schematic diagram illustrating a perspective view of an exemplary embodiment of an automatically activated scent diffuser.

Referring now to FIG. 5, a non-limiting exemplary embodiment 500 of the automatically activated scent diffuser 116 is illustrated, wherein the automatically activated scent diffuser 116 may include an aperture with an electrically activated fragrance shutter, wherein electric activation controls movement of the fragrance shutter. System 100 may preferably comprise a generally rectangular lower housing portion 504 which includes a compartment 508 for battery component for electrical power, including standard alkaline batteries such as size AA batteries, or a rechargeable battery equivalent, and an upper housing portion 512 which encloses circuitry and a mounting collar or fragrance holder 516 for receiving a generally cylindrical bottle 520 adapted to contain a fragrance liquid, fluid, oil, wax, or other suitable fragrance, scent, and/or aroma substance. Preferably, a lower peripheral rim 524 of the upper housing portion 512 mates with an upper peripheral rim 528 of the lower housing portion 301, and the two housing portions are secured together by screws 432, threaded through horizontal flanges 536 formed at respective corners of the peripheral rims. It will be apparent that alternative securing structures can be substituted for the screws, by those having ordinary skill in the art.

Continuing in reference to FIG. 5, the circuitry mounted in the upper housing portion 512 suitably comprises a voltage regulator 540 (for example, model D24V10F5 available from Pololu Corp of Las Vegas Nev., USA), a communications module, for example a BLUETOOTH transceiver 544 (such as SparkFun model nRF52832, available from SparkFun Electronics of Niwot, Colo., USA), an ultrasonic transducer printed circuit board (PCB) 548, a solenoid or linear actuator 552, and a solenoid control circuit 556 (available from Efcom of Rehovot, Israel). As in the case of ultrasonic transducers used in home humidifiers, PCB 548 drives a generally annular ultrasonic transducer arranged at an outlet opening of the bottle 520 of fragrance fluid; the transducer serves to nebulize the fluid, in order to emit the fragrance into the ambient air surrounding the user of the diffuser. Also mounted in upper housing portion 512 is the fragrance holder 516 for receiving the bottle 520 of fragrance fluid. On top of the bottle holder, there is pivotably secured a horizontally oriented shutter 560, formed with a vertical bore or hole 564. Horizontally oriented shutter 560 is mounted at a corner thereof for rotation on a vertically aligned solenoid pin, so that shutter 560 can be rotated, for example about 90 degrees, alternately in a first rotation direction and in a second rotation direction. The linear actuator 552 is mechanically coupled to the shutter 560, so that the shutter 560 serves as a valve, opening the bottle when the hole 564 in the shutter is aligned with a central opening 568 at the top of the bottle, and closing the bottle when the hole 564 has been pivoted sideways, out of alignment with the bottle central opening 568. It is important to note that the central opening is a hole in the outer housing that allows fragrance to escape when the hole 564 in the shutter 560 aligns with the central opening 568. In such a case, the central opening is located in the outer housing of the device, as illustrated in further detail below. Alternatively, the shutter can be pivoted by an electric servomotor (such as model FS90, available from FeeTech RC Model Co. Ltd. of Shenzhen, China).

Figure 6:
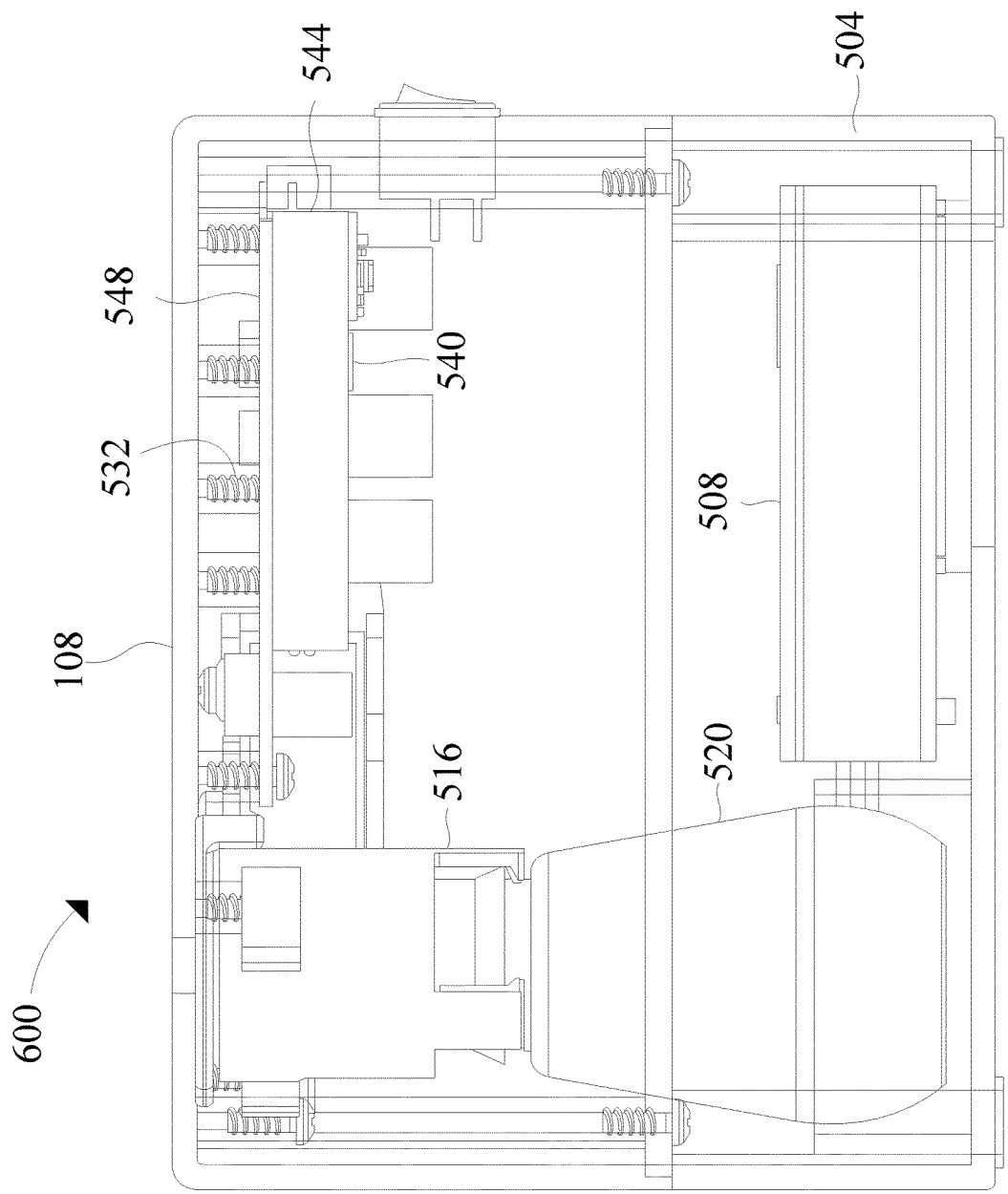
FIG. 6 is a diagrammatic representation of a side-view illustrating of an exemplary embodiment of an automatically activated scent diffuser.

Referring now to FIG. 6, a non-limiting exemplary embodiment of a side-view 600 of the automatically activated scent diffuser 108 is illustrated. Showing the housing port ions in phantom, in order to show an exemplary configuration of the bottle 520, the bottle holder 516 and the respective circuit boards. In the non-limiting exemplary embodiment, the battery compartment 508 is housed in the lower housing portion 504. Circuit power may be provided by a commercially available electrochemical battery, such as standard AA, AAA, 9-volt, and the like. Compatible energy sources may be photovoltaic cells configured to charge an energy storage system, like a battery pack, module, or the like. In general, photovoltaic cells cover a surface area or the device and/or charging station that a device may connect, wherein the photovoltaic cells may absorb incident light and is configured to eject free electrons present in the photovoltaic cells, generating a flow of electricity. Battery and/or battery cell may include, without limitation, Li ion batteries which may include NCA, NMC, Lithium iron phosphate (LiFePO4) and Lithium Manganese Oxide (LMO) batteries, which may be mixed with another cathode chemistry to provide more specific power if the application requires Li metal batteries, which have a lithium metal anode that provides high power on demand, Li ion batteries that have a silicon or titanite anode. The battery may include, without limitation a battery using nickel based chemistries such as nickel cadmium or nickel metal hydride, a battery using lithium ion battery chemistries such as a nickel cobalt aluminum (NCA), nickel manganese cobalt (NMC), lithium iron phosphate (LiFePO4), lithium cobalt oxide (LCO), and/or lithium manganese oxide (LMO), a battery using lithium polymer technology, lead-based batteries such as without limitation lead acid batteries, metal-air batteries, or any other suitable battery. A person of ordinary skill in the art, upon reviewing the entirety of this disclosure, will be aware of various devices of components that may be used as an energy storage device.

Continuing in reference to FIG. 6, the automatically activated scent diffuser 116 may include an ultrasonic transducer, wherein activation of the ultrasonic transducer disperses the fragrance. The circuitry mounted in the upper housing portion 512 suitably comprises a voltage regulator 540. Voltage regulator 540 may be any configuration of device used to automatically maintain a constant voltage level in providing electromechanical control to the communication module, actuators, and the like. Communications module may be any device used for transmitting a signal, as described above, for instance in non-limiting exemplary embodiments, a BLUETOOTH transceiver 544. The automatically activated scent diffuser 108 may include at least a printed circuit board (PCB) for mechanically supporting and electrically connecting electrically powered components within the device, such as an ultrasonic transducer printed circuit board (PCB) 548. The ultrasonic transducer PCB 548 may be affixed to the housing, for instance and without limitation, using screws as illustrated above.

Figure 7A:
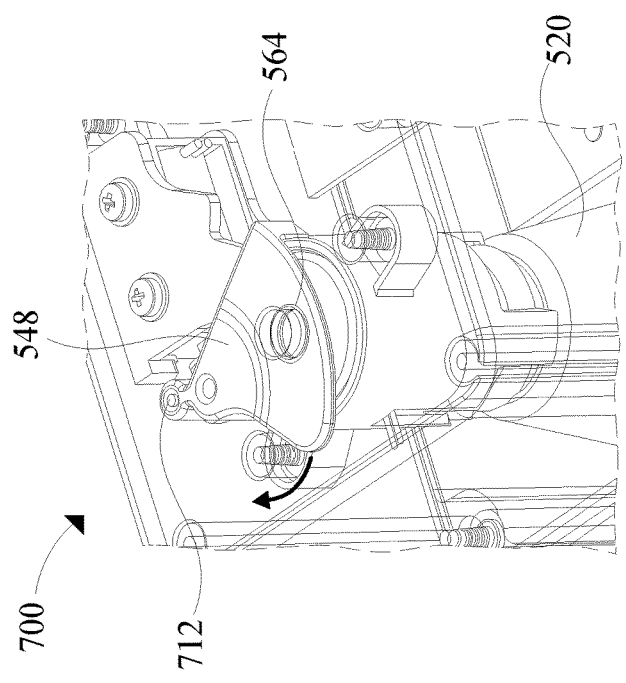
FIGS. 7A-7B is a schematic diagram illustrating a perspective view of an exemplary embodiment of an open automatically activated scent diffuser interior.
Figure 7B:
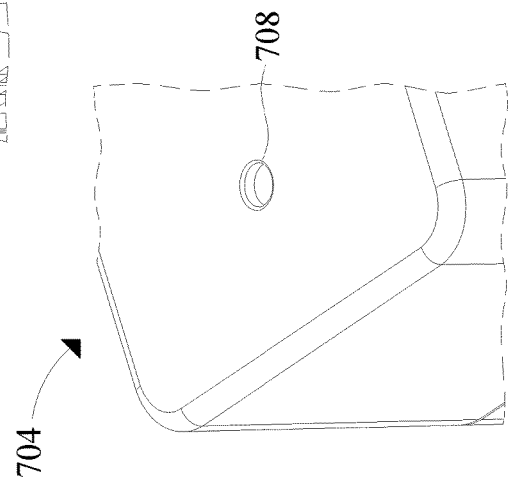

Referring now to FIG. 7A and FIG. 7B, the open automatically activated scent diffuser interior 700 and the open automatically activated scent diffuser exterior 704, respectively, are illustrated. Shutter 560 may be aligned to open the bottle 520 to release fragrance by pivoting, as denoted by the black arrow to align with the central hole 708 in the exterior housing pictured in FIG. 7B. The shutter 560 may move about a pivot 712, as indicated by the black arrow in FIG. 7A, from a closed resting position to the currently pictured aligned 'open' position. As shown as a non-limiting exemplary embodiment in FIG. 7A, shutter 560 may have a generally triangular shape with a pivot 712 at one vertex, subtending an angle of approximately 60 degrees. The hole 564 located in the shutter 560 may be formed through both faces of the triangular shutter to allow fragrance to exit the diffuser. Shutter 560 may rotate about the pivot 712 approximately 20 degrees for the hole 564 in the shutter 560 to fall out of alignment with the central hole 708, thereby bringing a solid portion of the shutter 560 adjacent to the central hole 708, closing the bottle 520.

Figure 8A:
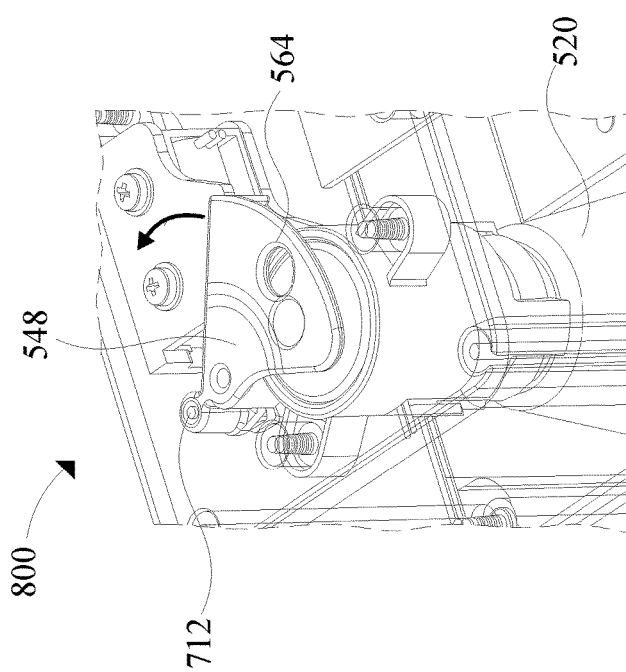
FIGS. 8A-8B is a schematic diagram illustrating a perspective view of an exemplary embodiment of the closed automatically activated scent diffuser interior.
Figure 8B:
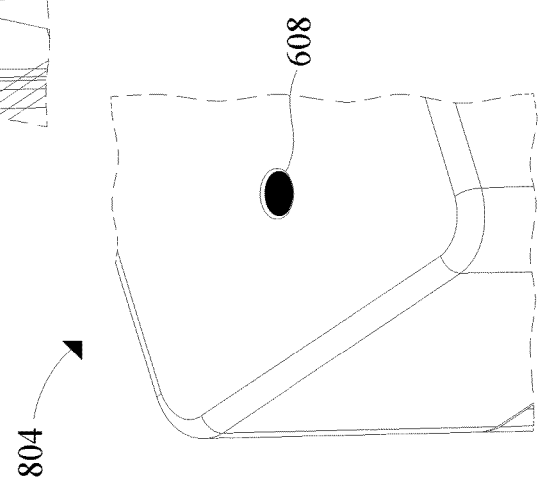

Referring now to FIG. 8A and FIG. 8B, the closed automatically activated scent diffuser interior 800 and the closed automatically activated scent diffuser exterior 804, respectively, are illustrated. FIGS. 8A and 8B show, respectively, the diffuser interior and diffuser exterior when shutter 520 is aligned to close bottle 520 by presenting a solid portion of shutter 560 to the central opening 708 of bottle 520. In the non-limiting exemplary embodiment, this movement is about the pivot 712 point in the direction denoted by the black arrow in FIG. 8A. Shutter 560 hole 564 moving approximately 60 degree in the direction of the black arrow may result in covering the central opening 708 in the exterior housing, resulting in closing the central opening 708, as denoted by the black shaded area in FIG. 8B.

Figure 9:
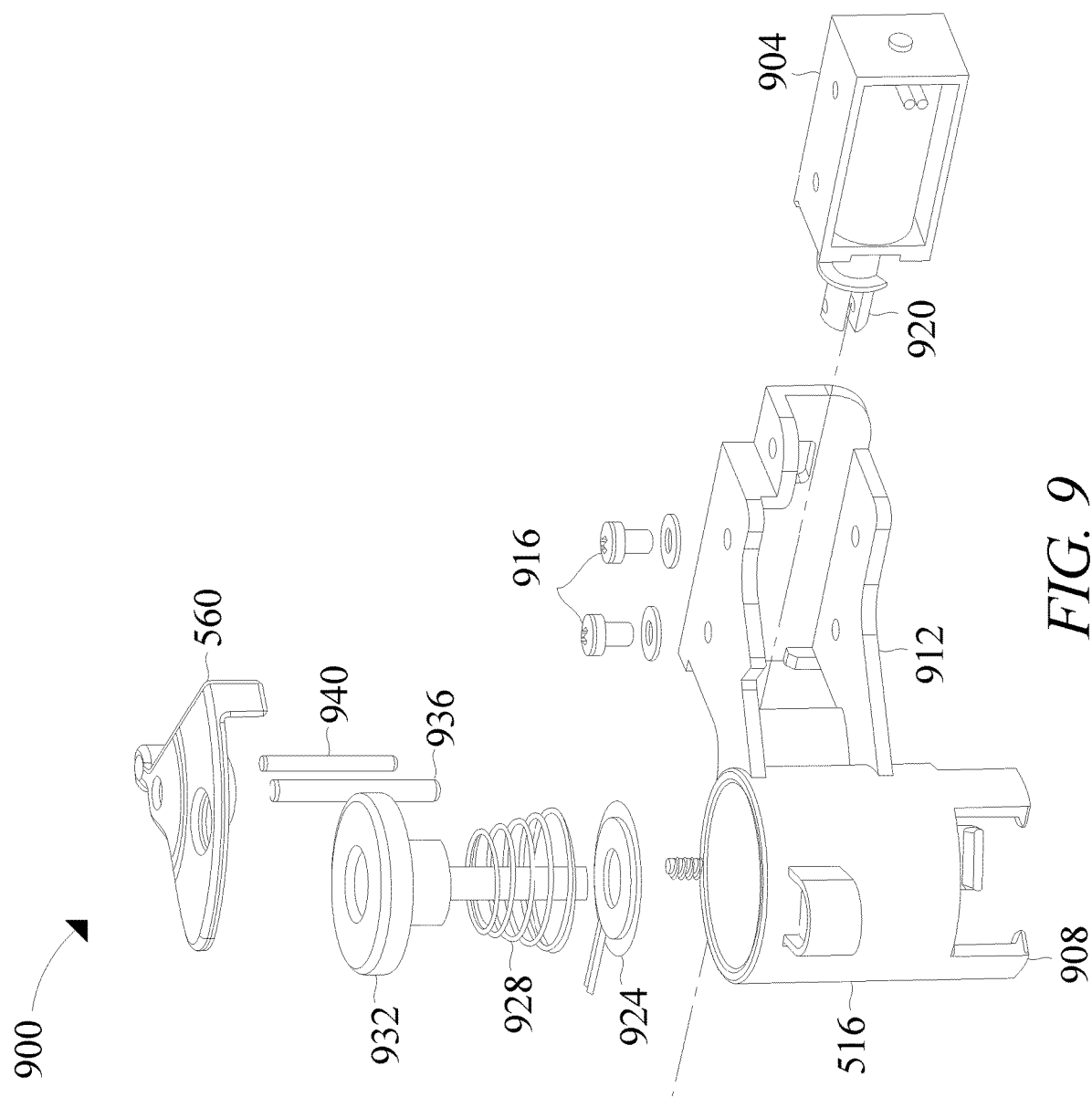
FIG. 9 is a schematic diagram illustrating an exploded view of an exemplary embodiment of a bottle holder and solenoid for fragrance release.

Referring now to FIG. 9, is a non-limiting exemplary embodiment in an exploded view 900 of a bottle holder 516 and solenoid 904 for fragrance release function in the automatically activated scent diffuser 116 is illustrated. Bottle holder 516 is preferably modeled of plastic, metal, or any other suitable material for purposes as described herein, forming a hollow vertical cylinder with a plurality of depending latches or claws 908 which in vertical cross-section may be 'L-shaped', for instance in non-limiting illustrative embodiments, three claws 908 separated at approximately 120-degrees circumferential intervals. Claws 908 may be pointed radially inward so that a bottle 520 may be held securely, even if an external force is applied to the entire diffuser structure. As a fragrance bottle 520 may be disposable, replaceable, or otherwise switched-out, bottle holder 516 may allow bottles 520 to be taken out and a new one replaced.

Continuing in reference to FIG. 9, bottle holder 516 is preferably formed with a laterally projecting 'U-shaped" channel 912 adapted to secure the solenoid 904. As shown in FIG. 9, channel 912 may preferably contain multiple surfaces, such as an upper horizontal surface, lower horizontal surface, and side vertical surface, which may in contact with the solenoid 908 to firmly securing the solenoid 908. Solenoid 908 may be further secured in channel 912 by solenoid screws 916. Solenoid 908 may be positioned within the channel 912, wherein the solenoid piston 920 is extended through the channel 912 open end (along dashed line).

Continuing in reference to FIG. 9, to facilitate evaporation and dispersion of scented oils, liquids, fluids, and the like, contained in a bottle 520, a generally, disk-shaped ultrasonic transducer 924 is provided, dimensioned to be received within the bottle holder 516. Ultrasonic transducer 924 may be the same as or like a nebulizer, aroma lamp, humidifier, or any other diffuser that may be used to generate an aerosolized spray of a liquid. Ultrasonic transducer 924 may be used for liquid dispersal by generating a spray, mist, and/or aerosolization, by using electrical current to generate vibrations, sonics, acoustics, or any other ultrasonic energy source, to generate fine dispersal droplets of a liquid, oil, colloidal suspensions, perfume, or the like, to spray droplets in an aimed direction. Such ultrasonic transducers are widely used in residential humidifying devices, and suitable models are well known to those having ordinary skill in the air treatment and fragrance dispensing arts. Transducer may be electronically driven by the ultrasonic transducer PCB 548. Alternatively or additionally, a fan may be provided to disperse scent droplets produced by an ultrasonic transducer 924. A coil spring 928 may be placed on top of the ultrasonic transducer 924. A leading tube 932 with a top annular flange is placed on top of spring 928, so that spring 928 may urge leading rube 932 upward toward shutter 560. This tends to minimize leakage of volatile chemical components of the fragrance fluid from bottle 520 at times when dispensing in not intended. As previously mentioned, a central pin 936 rides within another cylindrical sleeve which is secured to a bottom surface of shutter 560, and a solenoid pin 940 rides within another cylindrical sleeve connected by a bridge to the central pin's sleeve.

Figure 10:
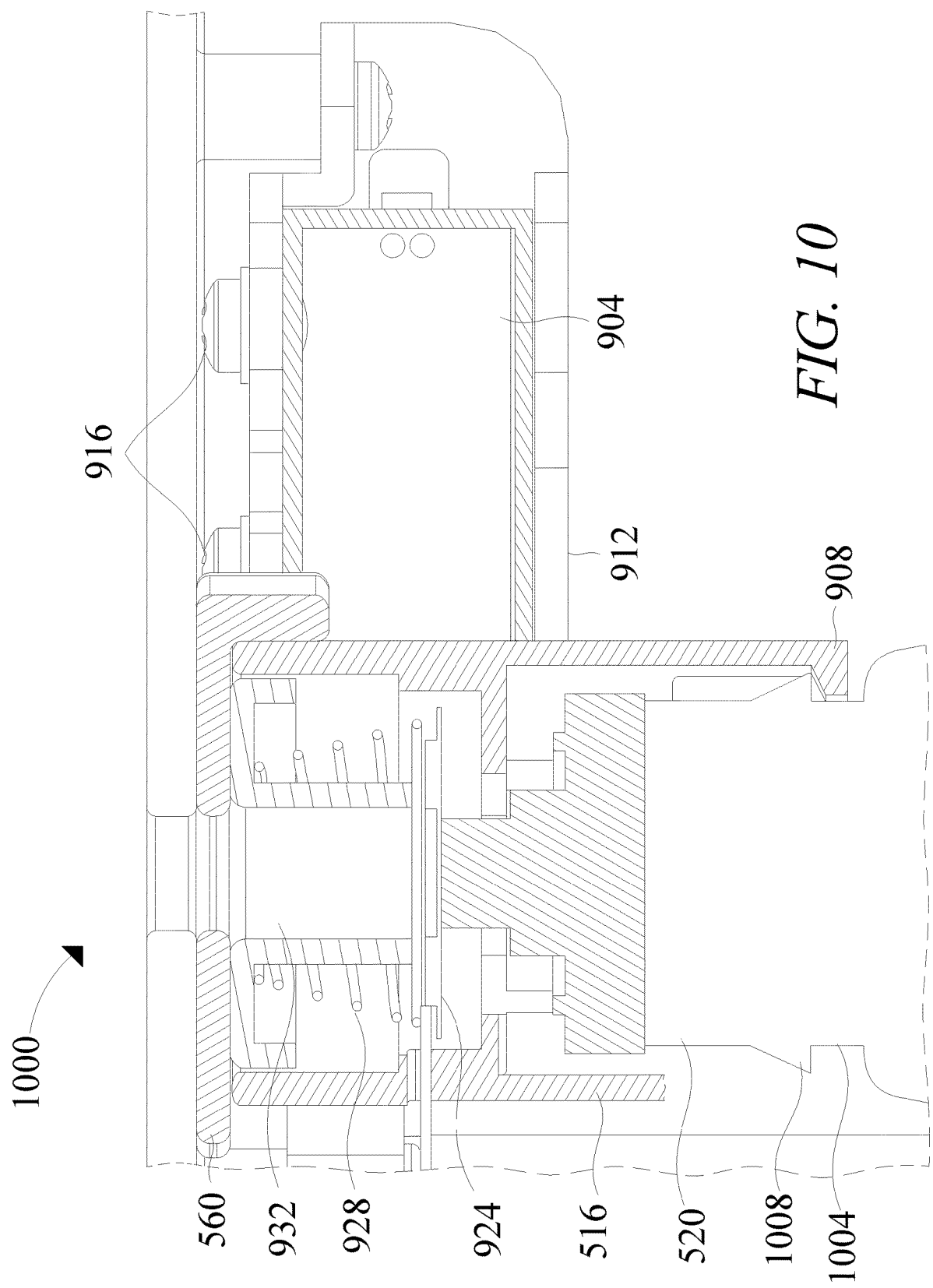
FIG. 10 is a diagrammatic representation of a cross-section of an exemplary embodiment of an assembled state of a bottle holder and solenoid for fragrance release.

Referring now to FIG. 10, a non-limiting exemplary embodiment in a cross-section 1000 showing components in an assembled state of a bottle holder 516 and solenoid 904 for fragrance release function in the automatically activated scent diffuser 116 is illustrated. Bottle 520 may be secured in the holder 516 by claws 908 clamped onto annular grooves recesses 1004 to facilitate secure gripping by the bottle holder 516. Bottle 520 may contain an annular collar 1008 to assist with securing into the bottle holder 516.

Figure 11A:
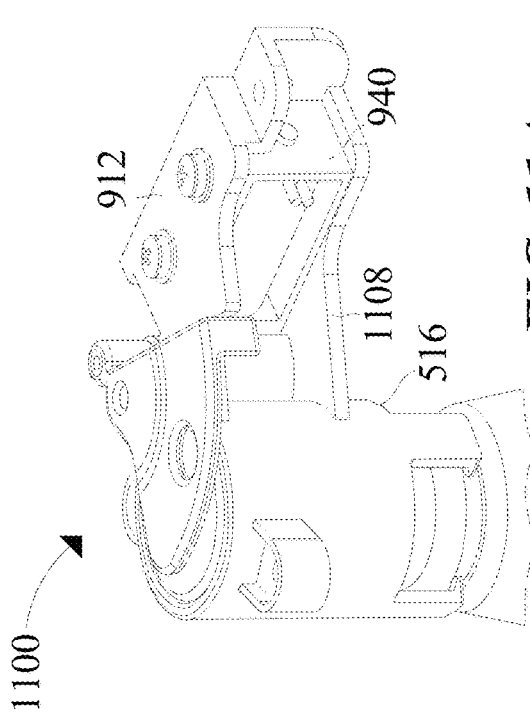
FIGS. 11A-11B is a schematic representation of an enlarged perspective view of an exemplary embodiment of a side face of solenoid, channel, and horizontal bridge.
Figure 11B:
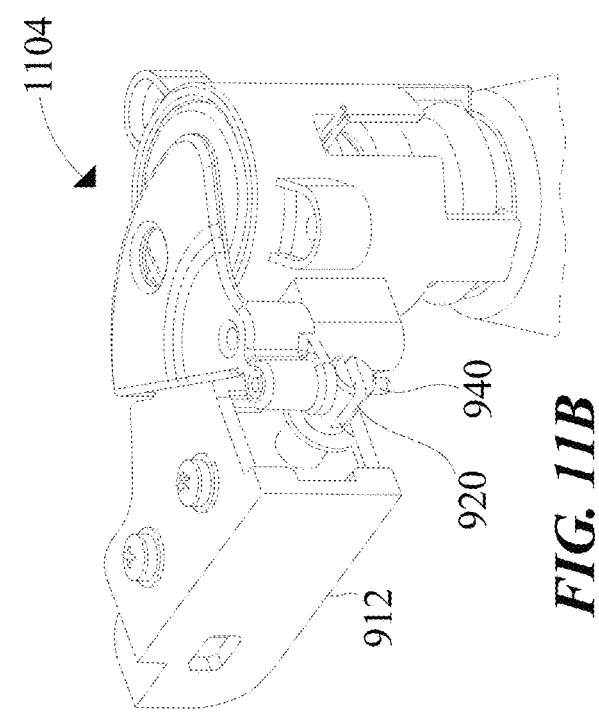

Referring now to FIG. 11A and FIG. 11B, a non-limiting exemplary embodiment of a slightly enlarged view showing a flat vertical side face 1100 of solenoid 904, channel 912, and horizontal bridge, and a 180-degree rotated view, respectively, is illustrated. Solenoid 904 may be secured into channel 912 which is connected to bottle holder 516 via a horizontal bridge 1104. As shown in FIG. 11B, solenoid piston 920 may follow through the open end of channel 912, as was denoted by the dashed line described above in FIG. 9, and extend out the other side, attaching to the solenoid pin 940.

Referring now to FIGS. 12A and 12B, a non-limiting exemplary embodiment of a solenoid piston 920 actuates shutter 560 to switch between a first, bottle-open configuration 1200, and a second, bottle-closed configuration 1204, respectively, is illustrated. A coupling 1208 between solenoid piston 920 and shutter 560 includes a vertically aligned central pin 936 and a vertically aligned solenoid pin 940. Central pin 936 and solenoid pin 940 are configured within their respective cylindrical sleeves, wherein the sleeves are rigidly connected to each other by the horizontal bridge 1008, connecting the solenoid channel 912 to the bottle holder 516. A lower end of solenoid pin 940 is received in a vertical bore formed in the solenoid piston 920. Energizing the coil within the solenoid 904 by applying electrical current may cause solenoid 904 to retract, or otherwise displace, solenoid piston 920, causing it to exert a pulling force inward towards the solenoid, as denoted by the black arrow in FIG. 12A. An annular stop 1212 on the exterior of the solenoid piston 920 may limit the distance of movement of the solenoid piston 920, as the annular stop 1212 comes into abutment with an end face of the solenoid piston 920. Central pin 936 may be fixed in a portion of the bottle holder 516 such that the horizontal bridge 1008 allows the sleeve around the central pin 936 to rotate (about the axis denoted by the vertical dashed line), further allowing shutter 560 to rotate clockwise (denoted by the curved arrow) until shutter hole 564 is vertically aligned with bottle opening, allowing scented fluid to be released from the bottle. Conversely, when solenoid 904 is de-energized as shown in FIG. 12B, solenoid piston 920 moves outwardly with respect to solenoid 904, as denoted by the black arrow, and horizontal bridge 1008 transmits this motion to the sleeve surrounding central pin 936, causing shutter 560 to rotate counter-clockwise, thereby closing bottle 520 and stopping release of scented fluid. In non-limiting exemplary examples, bottle 520 is preferably somewhat tapered, larger in diameter near the bottom, and formed near its top with a radially projecting annular collar 908, beneath which is an annular groove or recess 904, to facilitate secure gripping by bottle holder 516.

Referring now to FIG. 13, an exemplary embodiment of a method 1300 of inducing a Pavlovian conditioned association of an aroma with a state of weight reduction. At step 1305, system 100 includes detecting, by a physiological sensor, at least a physiological parameter of a user, wherein the at least a physiological sensor is configured to detect at least a physiological parameter of a user, and to transmit a detection signal. The physiological sensor transmits a detection signal to a control device; this may be implemented without limitation as described above in FIGS. 1-12.

At step 1310, and still referring to FIG. 13, system 100 includes identifying, by a control device, that the user is experiencing a physiological state associated with weight reduction. Identifying, by the control device, that the user is experiencing a physiological state associated with weight reduction may include determining that a detection signal corresponds to a physiological state of endorphin release. Identifying the physiological state associated with weight reduction may include determining a moment of refute, wherein the user is engaging in a behavior that contributes to weight gain and deactivating the automatically activated scent diffuser. A behavior that contributes to weight gain is a behavior a user exhibits that results in excessive energy availability. Identifying the physiological state associated with weight reduction may include determining a moment of clarity, wherein the user is engaging in a behavior that contributes to weight reduction. A behavior that contributes to weight reduction is a behavior a user exhibits that results in energy availability below weight maintenance levels; this may be implemented without limitation as described above in FIGS. 1-12.

Continuing in referring to FIG. 13, as used herein, "endorphin release", is endogenous endorphin-family neurotransmitters and/or neuromodulators and all precursor peptides, such as pro-opiomelanocortin (POMC) and the four endorphin types, alpha, beta, gamma, and sigma, and the physiological responses associated with endorphin signaling. In general, endorphin release is understood to be associated with the body's response to pain modulation and can also be associated with exercise such as a "runner's high." Additionally, endorphins have been found to be associated with states of pleasure exhibited during expression of emotions and behaviors brought upon by laughter, love, sexual intimacy, and satiation, among many others. Endorphin release has been observed to be related to activities associated with weight reduction, especially diet and exercise activities. Tracking the physiological and chemical events in response to endorphin signaling, such as changes in heart rate, blood pressure, flushed facial look, among others, may be achieved using physiological sensors, as described above. Endorphin release may be coupled to fragrance diffusion to generate a physiological, cognitive, and/or behavior response wherein recognition of the fragrance may be associated with the feelings, emotions, and behaviors of endorphin release. In non-limiting exemplary examples, supplying fragrance during tracked periods characterized by detection signals and/or biomarkers associated therewith, such as without limitation data indicating endorphin release, may generate a Pavlovian conditioning wherein applying the fragrance stimulus may be linked via conditioning to a mental, emotional, or other state conducive to actions that tend toward weight loss, such as a state of satiation to reduce overeating, a desire to engage in physical activity that builds muscle and/or burns calories, or the like.

Continuing in referring to FIG. 13, as used herein, "energy availability," is the clinical terminology that is the amount of energy taken in by a user minus the amount of energy expended in a user. Energy availability may be essentially the number of calories taken in minus the amount of caloric content required for basal metabolism and to complete exercise, tasks, etc., in a defined period, such as over a day. In non-limiting illustrative examples, energy availability may be logged by a user, for instance, via a user device, mobile app, web browser, or the like, and energy expenditure may be logged by a user in a similar manner. User energy intake and energy expenditure may be mapped to physiological sensor data using a computing device 112, for instance and without limitation as in the control device 108, as described above. Energy intake and energy availability may be metrics used in calculating energy availability and thus gauging the behaviors contributing to weight reduction and further informing the use of the fragrance diffusion.

Continuing in referring to FIG. 13, as used in this disclosure, "behavior that contributes to weight gain," is any user behavior, action, effort, task, or the like, carried out by the user that is identified by physiological sensors, as described above, that is associated with weight gain. Weight gain behaviors may not be universal and may differ between users. In non-limiting illustrative examples, behaviors that contribute to weight gain may involve excessive energy intake, such as overeating, eating calorie-dense foods in place of lower caloric density foods, eating too frequently, eating infrequently, and/or erratic feeding patterns, lack of exercise, poor exercise habits, among other behaviors. In such an example, scent diffusion may be associated with normalized eating patterns, lower caloric density food replacements, and the like, to combat behaviors that contribute to weight gain, or even replace the behaviors altogether.

Continuing in referring to FIG. 13, as used in this disclosure, "behavior that contribute to weight reduction," is any user behavior, action, effort, task, or the like, carried out by the user that is identified by physiological sensors, as described above, that is associated with weight reduction. Weight reductions behaviors may not be universal and may differ between users. In non-limiting illustrative examples, behaviors that contribute to weight reductions may involve increases in energy expenditure and/or reduction of energy intake, such as exercising, replacing calorie-dense foods with lower caloric density foods, eating less frequently, eating more regularly, fasting, among other behaviors. In such an example, scent diffuser may be associated with exercise such as hiking, and/or scent diffuser may be performed every hour of fasting after a certain time period to train a person to feel satiated, less hungry, more fulfilled, or the like, in training to abstain from overeating by rewarding lower energy intake.

Still referring to FIG. 13, as used in this disclosure, "moment of refute," is any moment when a user is engaging in a behavior, action, effort, task, or the like, carried out by the user that is identified by physiological sensors that is associated with weight gain, when the user could otherwise engage in behavior that is productive towards weight reduction. A moment of refute may be a period of decision making for a user after which a user may engage in a behavior that is counter-productive towards weight reduction. Computing device 104 may determine such moments of refute by analyzing physiological sensor 104 detection signals transmitted via a control device 108. Alternatively or additionally, computing device 104 may determine moments of clarity, as described above, from user questionnaire data, user input data, user caloric tracking data, user exercise data, and the like, that is user-originated data that described behaviors productive toward weight reduction, wherein the physiological sensor data may be further analyzed with indications of these events. For instance a moment of refute that may be identified for activation of scent diffusion may be when a user is eating a caloric excess by choosing caloric-dense foods on days when the user is already at considerable excess energy availability. Physiological sensor 104 data may determine a user is eating, but not to dispense an aroma due to the user opting to engage in counter-productive behaviors during and following a moment of refute.

At step 1315, and still referring to FIG. 13, system 100 includes dispensing a scent by an automatically activated scent diffuser 116 as a function of the user experiencing the physiological state associated with weight reduction. Dispensing the scent by the automatically activated scent diffuser 116 may include transmitting, by the control device 108, an actuation signal to the automatically activated scent diffuser 116 at a time when the user is engaging in a behavior that contributes to weight reduction. Control device 108 displays, to the user, information regarding the automatically activated scent diffuser 116 usage. The control device 108 is activated by the user to dispense a scent, wherein the scent is identical to the scent dispensed by the automatically activated scent diffuser. The scent is diffused by user activation prior to a user experiencing a moment of refute, wherein the scent guides the user from engaging in the moment of refute; this may be implemented without limitation as described above in FIGS. 1-12.

Figure 14:
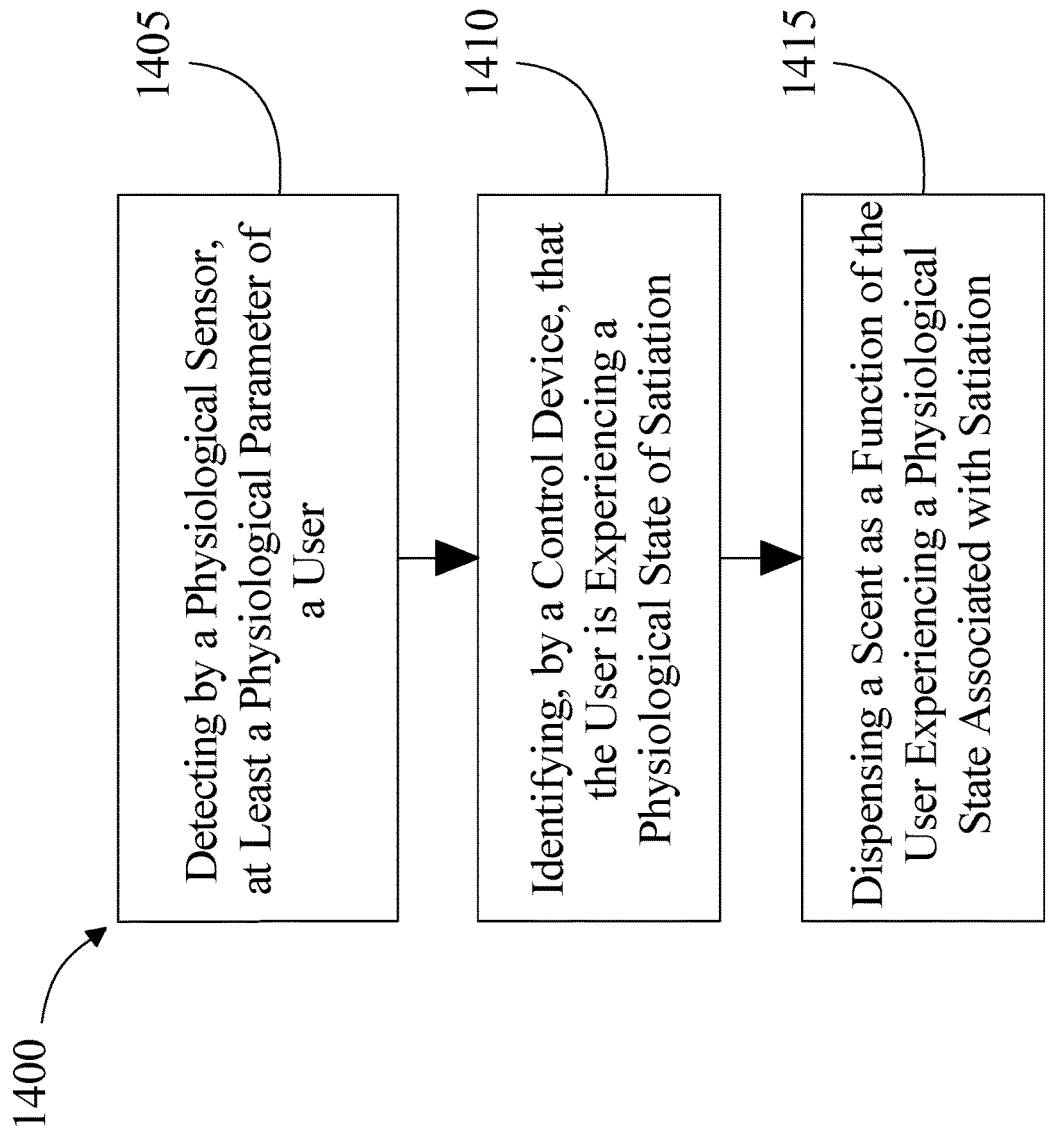
FIG. 14 is a flow diagram illustrating an exemplary method for conditional satiation.

Referring now to FIG. 14, an exemplary embodiment of a method 1400 of inducing a Pavlovian conditioned association of an aroma with a state of satiation is illustrated. Pavlovian conditioned association of an aroma with a state of satiation may be used to identify physiological patterns corresponding to satiation using at least a physiological sensor and the computing device 104 and to supply an aroma so that a user may experience satiation without consuming food. Satiation may be felt after an individual eats a meal until feeling satisfied and no longer hungry, and thus satiation may be reached by consuming an adequate amount of food in a specific period of time. Satiation may be marked by several emotional, psychological, digestive, and physiological patterns that can be recognized by questionnaire data pertaining to a user, as well as physiological sensor parameters. Identified physiological patterns may be used to create an association between a physiological state, such as satiation, with a specific scent, leading to a Pavlovian conditioned response in the user. In this way, a user may stop themselves from engaging in behaviors that contribute to weight gain, such as overeating at any meal, by exposing themselves to the scent they were conditioned to associate with satiation, wherein olfactory stimulation of the scent leads to satiety. This may then lead a user to eat less and more easily adhere to a weight reduction strategy. At step 1305, system 100 includes detecting, by a physiological sensor, at least a physiological parameter of a user, wherein the at least a physiological sensor is configured to detect at least a physiological parameter of a user, and to transmit a detection signal. The physiological sensor transmits a detection signal to a control device; this may be implemented without limitation as described above in FIGS. 1-13.

Further referring to FIG. 14, physiological response associated with satiation may be detected by at least a physiological sensor. A physiological response may include physiological biomarkers, including without limitation broad spectrum biomarkers and/or narrow spectrum biomarkers as defined above. A physiological response associated with satiation may be due to a gastric mechanism of satiation and/or intestinal mechanism of satiation, either or both of which may signal directly with the central nervous system to control hunger and eating behaviors. A gastric mechanism of satiation may involve mechanosensing of mechanical cues, such as distention of gut organs such as the stomach, which may result in a signal being transmitted through the vagus nerve, wherein gastric distension is a physiological biomarker of satiation. An intestinal mechanism of satiation may involve gut hormones, peptides, and/or other signaling molecules released from gastrointestinal tract organs that communicate with the brain. Physiological biomarkers involved in gut signaling of these two mechanism to trigger feelings of satiation may include decreased ghrelin release from the stomach to reduced feelings of hunger; increased cholecystokinin (CCK) released from the duodenum and jejunum which signals through the vagus nerve, stimulating pancreatic enzyme secretion and gall bladder contraction; increased glucagon-like peptide-1 (GLP-1) and oxyntomodulin (OXM) which are signaling peptides released by the intestines that act on receptors in the brain to slow gastric emptying and stimulate insulin production; peptide YY (PYY) released from the ileum, colon, and rectum which binds the Y2 receptor in the brain to slow gastric emptying and increase intestinal transport of nutrients; and/or pancreatic polypeptides which bind via the Y5 receptors in the brain and via the vagus nerve to signal for satiety, among other hormones, peptides, and other signaling molecules involved in satiation. Each of the above-described biomolecules may be physiological biomarkers used for determining if a user is experiencing satiation. Machine-learning methods may be assisted with user questionnaire data that can more precisely place the timing of eating with the detection of the biomarkers.

Continuing in reference to FIG. 14, it may be observed that signaling through the hormones, peptides, and the like, released by the gastrointestinal tract organs, as described above, communicate with the central nervous system and endocrine systems, including the brain, adrenal gland, pituitary gland, among other organs, and contributes to feelings of satiety. For instance, signaling to the brain that gastric distention has occurred from a full stomach may lead to stimulating the brain's endogenous opioid system to signal pleasure, appetite, and satiety. Such signaling may trigger the endogenous opioid system to release endorphins through the pituitary gland, as described herein. Physiological changes that may be detected by a physiological sensor relating to endorphin released may include pain reduction, reduced stress, slowed breathing, decreased blood pressure, decreased heart rate, among others.

Continuing in reference to FIG. 14, at step 1410, system 100 includes identifying, by a control device, that the user is experiencing a physiological state associated with satiation. Identifying, by the control device, that the user is experiencing a physiological state associated with satiation may include determining that a detection signal corresponds to a physiological state of endorphin release related with eating. Identifying the physiological state associated with satiation may include determining a moment of refute, wherein the user is engaging in a behavior that contributes to weight gain and deactivating the automatically activated scent diffuser. A behavior that contributes to weight gain is a behavior a user exhibits that results in excessive energy availability. Identifying the physiological state associated with satiation may include determining a moment of clarity, wherein the user is engaging in a behavior that contributes to weight reduction. A behavior that contributes to weight reduction is a behavior a user exhibits that results in energy availability below weight maintenance levels; this may be implemented without limitation as described above in FIGS. 1-13.

At step 1415, and still referring to FIG. 14, system 100 includes dispensing a scent by an automatically activated scent diffuser 116 as a function of the user experiencing the physiological state associated with satiation. Dispensing the scent by the automatically activated scent diffuser 116 may include transmitting, by the control device 108, an actuation signal to the automatically activated scent diffuser 116 at a time when the user is engaging in a behavior that contributes to satiation. Control device 108 displays, to the user, information regarding the automatically activated scent diffuser 116 usage. The control device 108 is activated by the user to dispense a scent, wherein the scent is identical to the scent dispensed by the automatically activated scent diffuser. The scent is diffused by user activation prior to a user experiencing a moment of refute, wherein the scent guides the user from engaging in the moment of refute; this may be implemented without limitation as described above in FIGS. 1-13.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 15:
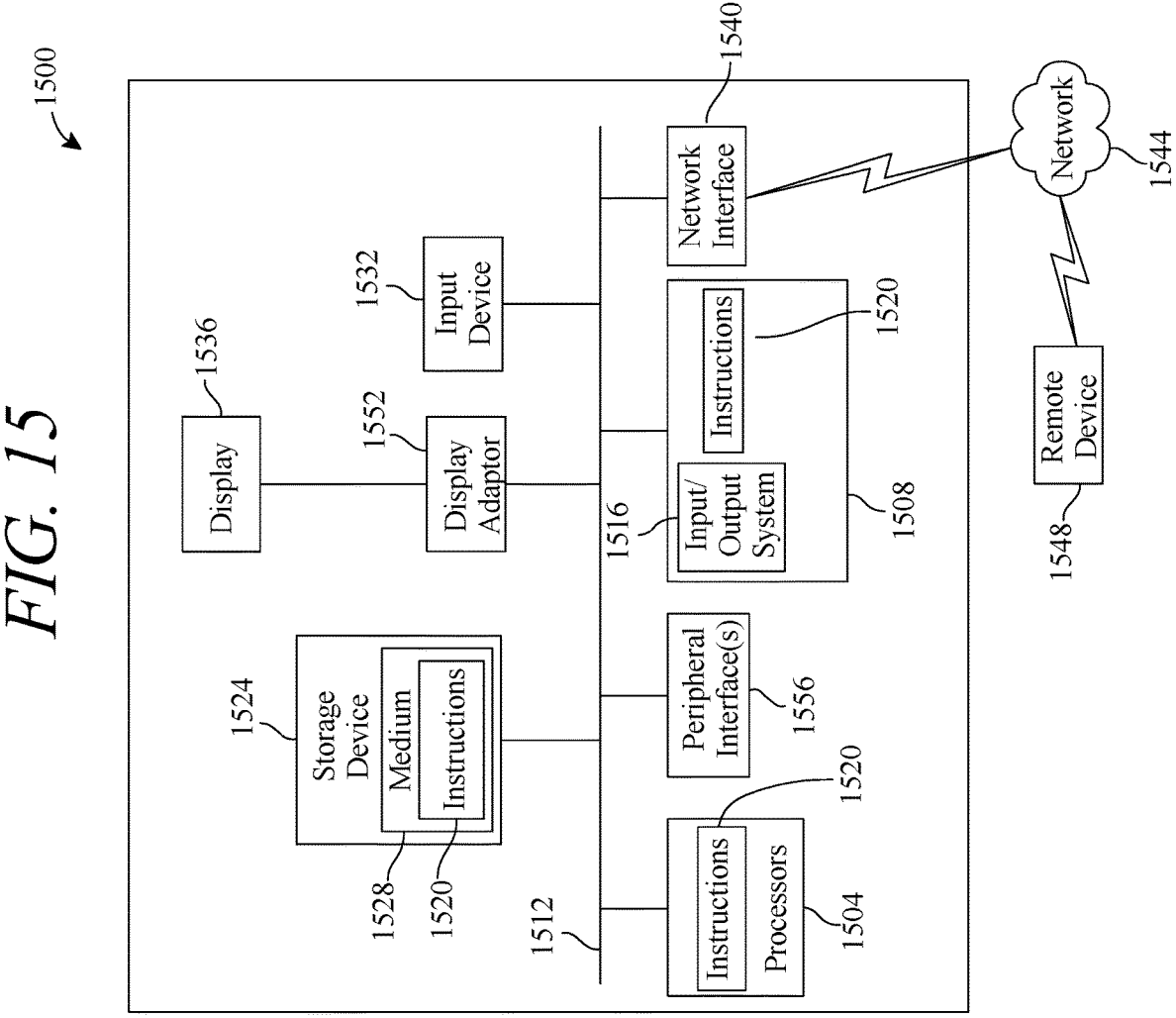
FIG. 15 is a block diagram of a computing system that can be used to implement any one or more of the methodologies disclosed herein and any one of more portions thereof.

FIG. 15 shows a diagrammatic representation of one embodiment of a computing device in the exemplary form of a computer system 1500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1500 includes a processor 1504 and a memory 1508 that communicate with each other, and with other components, via a bus 1512. Bus 1512 may include any of several types of bus structures including, but not limited to, a memory bus, a memory controller, a peripheral bus, a local bus, and any combinations thereof, using any of a variety of bus architectures.

Processor 1504 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1504 may be organized according to Von Neumann and/or Harvard architecture as a non-limiting example. Processor 1504 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 1508 may include various components (e.g., machine-readable media) including, but not limited to, a random-access memory component, a read only component, and any combinations thereof. In one example, a basic input/output system 1516 (BIOS), including basic routines that help to transfer information between elements within computer system 1500, such as during start-up, may be stored in memory 1508. Memory 1508 may also include (e.g., stored on one or more machine-readable media) instructions (e.g., software) 1520 embodying any one or more of the aspects and/or methodologies of the present disclosure. In another example, memory 1508 may further include any number of program modules including, but not limited to, an operating system, one or more application programs, other program modules, program data, and any combinations thereof.

Computer system 1500 may also include a storage device 1524. Examples of a storage device (e.g., storage device 1524) include, but are not limited to, a hard disk drive, a magnetic disk drive, an optical disc drive in combination with an optical medium, a solid-state memory device, and any combinations thereof. Storage device 1524 may be connected to bus 1512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1524 (or one or more components thereof) may be removably interfaced with computer system 1500 (e.g., via an external port connector (not shown)). Particularly, storage device 1524 and an associated machine-readable medium 1528 may provide nonvolatile and/or volatile storage of machine-readable instructions, data structures, program modules, and/or other data for computer system 1500. In one example, software 1520 may reside, completely or partially, within machine-readable medium 1528. In another example, software 1520 may reside, completely or partially, within processor 1504.

Computer system 1500 may also include an input device 1532. In one example, a user of computer system 1500 may enter commands and/or other information into computer system 1500 via input device 1532. Examples of an input device 1532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1532 may be interfaced to bus 1512 via any of a variety of interfaces (not shown) including, but not limited to, a serial interface, a parallel interface, a game port, a USB interface, a FIREWIRE interface, a direct interface to bus 1512, and any combinations thereof. Input device 1532 may include a touch screen interface that may be a part of or separate from display 1536, discussed further below. Input device 1532 may be utilized as a user selection device for selecting one or more graphical representations in a graphical interface as described above.

A user may also input commands and/or other information to computer system 1500 via storage device 1524 (e.g., a removable disk drive, a flash drive, etc.) and/or network interface device 1540. A network interface device, such as network interface device 1540, may be utilized for connecting computer system 1500 to one or more of a variety of networks, such as network 1544, and one or more remote devices 1548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1544, may employ a wired and/or a wireless mode of communication. In general, any network topology may be used. Information (e.g., data, software 1520, etc.) may be communicated to and/or from computer system 1500 via network interface device 1540.

Computer system 1500 may further include a video display adapter 1552 for communicating a displayable image to a display device, such as display device 1536. Examples of a display device include, but are not limited to, a liquid crystal display (LCD), a cathode ray tube (CRT), a plasma display, a light emitting diode (LED) display, and any combinations thereof. Display adapter 1552 and display device 1536 may be utilized in combination with processor 1504 to provide graphical representations of aspects of the present disclosure. In addition to a display device, computer system 1500 may include one or more other peripheral output devices including, but not limited to, an audio speaker, a printer, and any combinations thereof. Such peripheral output devices may be connected to bus 1512 via a peripheral interface 1556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for inducing a Pavlovian conditioned association of an aroma with a state of satiation, the system comprising:
    at least a physiological sensor, wherein the at least a physiological sensor is configured to detect at least a physiological parameter of a user, and to transmit a detection signal;
    a control device configured to receive the detection signal from the at least a physiological sensor, wherein the control device is further configured to:
        receive training data correlating physiological sensor data to several distinct states of the user; and
        train a machine-learning model with the training data, wherein the machine-learning model is configured to receive the physiological parameter and output a distinct state of the user, and wherein the machine-learning model is configured to sample the physiological sensor data in real-time to output a determination of the user's behavioral engagement; and
        ascertain that the user is experiencing a physiological state associated with satiation as a function of the machine-learning model, and transmit the detection signal to an automatically activated scent diffuser, thereby conditioning the user to associate said scent with satiation; and
    the automatically activated scent diffuser, wherein the scent diffuser is configured to automatically activate upon receiving the detection signal, wherein automatically activating further comprises diffusing a scent in response to the detection signal.

2. The system of claim 1, wherein ascertaining that the user is experiencing the physiological state associated with satiation further comprises determining that a detection signal corresponds to a physiological state of endorphin release.

3. The system of claim 1, wherein the control device is further configured to:
    determine a moment of refute, wherein the user is engaging in a behavior that contributes to weight gain; and
    deactivate the automatically activated scent diffuser.

4. The system of claim 3, wherein the behavior that contributes to weight gain is a behavior a user exhibits that results in excessive energy availability.

5. The system of claim 1, wherein the automatically activated scent diffuser further comprises a user activation control, wherein the user activates the scent diffuser as a function of the user activation control to diffuse an identical scent diffused by the automatically activated scent diffuser.

6. The system of claim 1, wherein the control device is further configured to:
provide a display to a user; and
display a message relating to the physiological state.

7. The system of claim 1, wherein the control device is further configured to accept a user input command control.

8. The system of claim 1, wherein the automatically activated scent diffuser is further configured to house a fragrance container.

9. The system of claim 1, wherein the automatically activated scent diffuser further comprises an aperture with an electrically activated fragrance shutter, and wherein an electric activation control moves the fragrance shutter.

10. The system of claim 1, wherein the automatically activated scent diffuser further comprises an ultrasonic transducer, wherein activation of the ultrasonic transducer disperses a fragrance.

11. A method of inducing a Pavlovian conditioned association of an aroma with a state of satiation, the method comprising:
detecting, by a physiological sensor, at least a physiological parameter of a user;
identifying, by a control device, that the user is experiencing a physiological state associated with satiation, wherein identifying comprises:
receiving training data correlating physiological sensor data to several distinct states of the user; and
training a machine-learning model with the training data, wherein the machine-learning model is configured to receive the physiological parameter and output a distinct state of the user, and wherein the machine-learning model is configured to sample the physiological sensor data in real-time to output a determination of the user's behavioral engagement;
ascertaining that the user is experiencing a physiological state associated with satiation as a function of the machine-learning model; and
dispensing a scent, by an automatically activated scent diffuser, as a function of the user experiencing the physiological state associated with satiation.

12. The method of claim 11, wherein identifying that the user is experiencing a physiological state associated with satiation further comprises determining that a detection signal corresponds to a physiological state of endorphin release.

13. The method of claim 11 further comprising:
determining a moment of refute, wherein the user is engaging in a behavior that contributes to weight gain; and
deactivating the automatically activated scent diffuser.

14. The method of claim 13, wherein the behavior that contributes to weight gain is a behavior a user exhibits that results in excessive energy availability.

15. The method of claim 11, wherein identifying the at least a physiological state associated with satiation further comprises determining a moment of clarity, wherein the user is engaging in a behavior that contributes to satiation.

16. The method of claim 15, wherein the behavior that contributes to satiation is a behavior a user exhibits that results in energy availability below weight maintenance levels.

17. The method of claim 11, wherein dispensing the scent by the automatically activated scent diffuser further comprises transmitting, by the control device, an actuation signal to the automatically activated scent diffuser at a time when the user is engaging in a behavior that contributes to satiation.

18. The method of claim 11, wherein the control device displays, to the user, information regarding the automatically activated scent diffuser usage.

19. The method of claim 11, wherein the control device is activated by the user to dispense a scent, wherein the scent is identical to the scent dispensed by the automatically activated scent diffuser.

20. The method of claim 11, wherein the scent is diffused by user activation prior to a user experiencing a moment of refute, and wherein the scent guides the user from engaging in the moment of refute.

* * * * *